(12) United States Patent
Brocchetta et al.

(10) Patent No.: US 6,337,064 B1
(45) Date of Patent: Jan. 8, 2002

(54) MANGANESE CHELATES WITH HIGH RELAXIVITY IN SERUM

(75) Inventors: Marino Brocchetta; Luisella Calabi; Daniela Palano; Lino Paleari; Fulvio Uggeri, all of Milan (IT)

(73) Assignee: Dibra S.p.A., Milan (IT)

( * ) Notice: Subject to any disclaimer, the term of this patent is extended or adjusted under 35 U.S.C. 154(b) by 0 days.

(21) Appl. No.: 09/601,576

(22) PCT Filed: Mar. 8, 1999

(86) PCT No.: PCT/EP99/01490

§ 371 Date: Sep. 25, 2000

§ 102(e) Date: Sep. 25, 2000

(87) PCT Pub. No.: WO99/45967

PCT Pub. Date: Sep. 16, 1999

(30) Foreign Application Priority Data

Oct. 3, 1998 (IT) .......................... MI98A0476

(51) Int. Cl.⁷ ............... A61K 49/10; C07C 229/28; C07C 229/36; C07D 209/20
(52) U.S. Cl. ............... 424/9.364; 424/9.365; 548/403; 548/455; 556/50; 562/445; 562/447; 562/500
(58) Field of Search .................. 548/403, 455; 556/50; 562/445, 447, 500; 424/9.364, 9.365

(56) References Cited

U.S. PATENT DOCUMENTS 4,980,148 A    12/1990    Dean 5,182,370 A  * 1/1993  Felder et al. ............... 534/16

FOREIGN PATENT DOCUMENTS

| EP | 0 230 893 | 8/1987 |
| EP | 0 279 307 | 8/1988 |
| WO | 98 05625 | 2/1998 |
| WO | 98 05626 | 2/1998 |

OTHER PUBLICATIONS

Keana, John F. W. et al: "Chelating ligands functionalized for facile attachment to biomolecules. A convenient route to 4-isothiocyanatobenzyl derivatives of diethylenetriaminepentaacetic acid and ethylenediamineteraacetic acid" J. Org. Chem. (1990), 55(9), 2868–71 CODEN: JOCEAH:ISSN: 0022–3263.

Westerberg, David A. et al: "Synthesis of novel bifunctional chelators and their use in preparing monoclonal antibbody conjugates for tumor targeting" J. Med. Chem. (1989), 32 (1), 236–43 CODEN: JMCMAR: ISSN: 0022–2623.

\* cited by examiner

*Primary Examiner*—Fiona T. Powers
(74) *Attorney, Agent, or Firm*—Nixon & Vanderhye

(57) ABSTRACT

Compounds of formula (I) both in the racemic and optically active forms, are used in MRI diagnostic imaging.

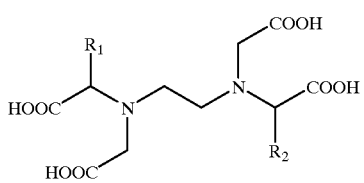

(I)

19 Claims, No Drawings

MANGANESE CHELATES WITH HIGH RELAXIVITY IN SERUM

The present invention relates to novel chelating agents and the manganese chelated complex salts thereof, the physiologically compatible salts thereof and the use of these compounds in magnetic resonance imaging (MRI).

A valuable M.R.I. contrast agent should recognizedly have, in addition to low administration dosages, very good relaxivity, so as to provide a suitable increase in the contrast between lesions and healthy tissue and among the different organs and tissues; high thermodynamic stability; slow transmetallation kinetic, in particular with ions of endogenous metals such as magnesium and calcium; low toxicity and very good tolerability. The gadolinium chelated complexes are at present the preferred contrast agents, due to the properties of $Gd^{3+}$ ion which has seven discoupled electrons and the highest magnetic moment. At the present time, commercially available contrast agents containing gadolinium chelated complexes are: Magnevist(R) (Gd-DTPA meglumine double salt), Dotarem(R) (Gd-DOTA meglumine salt), Omniscan(R) (Gd-DTPA-BMA) and ProHance(R) (Gd-HP-DO3A).

The more recent searches aim at founding contrast agents which, besides having the above cited characteristics, are also specific for a definite tissue or body region. Manganese has been suggested as an alternative to gadolinium in these tissue-specific contrast agents (Investigative Radiology 1995, 30(10), 611–620).

The potential usefulness of the $Mn^{2+}$ ion as an M.R.I. contrast agent has been taken in consideration since 1978 for myocardium imaging. Manganese complexes with porphyrines and derivatives thereof (for example Mn(III)-meso-tetra-(4-sulfonatophenyl)porphyrine, $Mn-TPPS_4$) were proposed as contrast agents specific for tumors (Investigative Radiology, cited ref.). In Magnetic Resonance in Medicine 1988, 8, 293–313, the longitudinal proton relaxation times in rabbit tissues have been studied after intravenous administration of $MnCl_2$ and of Mn-PDTA (1,3-propylenediamino-N,N',N'',N'''-tetraacetate). In a recent study, M.R.I. contrast agents were evaluated consisting of Mn-EDTA lipohilic derivatives (for example, manganese-EDTA-bis(hydroxypropyldecylamine), Mn-EDTA-DDP) bound to the membranes of small unilamellar liposomes ("memsomes"), which are potentially valuable for hepatic and cardiac perfusion imaging (Journal of Liposome Research 1994, 4(2), 811–834). The same compounds are object of International Patent Application WO 92/21017 and of U.S. Pat. No. 5,312,617, which disclose M.R.I. contrast agents based on manganese chelates (II) consisting of EDTA bis-amides where the amide nitrogens are substituted with long chain alkyl residues ($C_7$–$C_{30}$). These chelates per se or, more preferably, in combination with lipids or liposomes, are reportedly particularly useful for imaging of liver and as blood-pool agents.

M.R.I. contrast agents comprising manganese chelated complexes are also described in U.S. Pat. Nos. 4,980,148 and 5,246,696. Said complexes, in which the ligand is an alkylenediaminotetraacetic acid in which the alkylene chain is interrupted by one or more substituents selected from O, S, CHOH, CHSH, are stated to be particularly useful for imaging of liver, kidneys, pancreas and gastrointestinal tract.

Recently, Teslascan(R) (manganese complex of N,N'-1,2-ethanediylbis[N-[[3-hydroxy-2-methyl-5-[(phosphonooxy)methyl]-4-pyridinyl]-methyl]glycine salified with $Na^+$ (1:3), mangafodipir trisodium, was marketed in Europe and in the U.S.A. for use in M.R.I. of the liver. This compound was considered useful for M.R.I. diagnosis of pancreas adenocarcinoma and pancreatitis (Investigative Radiology 1995, 30(10), 611–620).

Ions of paramagnetic metals are known to be highly toxic. The same applies for $Mn^{2+}$ ion at the doses commonly used for diagnostic imaging, although this is an essential oligoelement, present in all mammal cells.

It is therefore important also in the case of manganese, for this to be administered as stable complex, thereby preventing any toxicity due to the free metal. Conversely, some compounds of the above cited literature, for example Mn-DPDP, show some instability in vivo: a recent biodistribution study proved that this complex dissociates, releasing manganese which accumulates in liver, pancreas and kidneys, whereas the undissociated chelate is removed through glomerular filtration. The M.R.I. properties of Mn-DPDP would therefore be ascribable mainly to the manganese ion released by the complex, which accumulates in liver and pancreas (Investigative Radiology 1994, 29(2), S249–S250). Another recent study gave evidence of the dissociation of Mn-DPDP in liver homogenate, in the presence of calcium and magnesium ions (MRM 1996, 35, 14–19).

The present invention relates to stable manganese chelated complex salts in which said ion is in the oxidation state +2 (Mn(II)). Said compounds are ethylenediaminotetraacetic acid (EDTA) derivatives, characterized in having a substituent containing at least one cyclic unit in α position to the carboxyl of one or two of the four acetic groups. Contrary to the manganese chelated complexes of the prior art, which, as mentioned above, are generally considered particularly useful in imaging of liver, pancreas and gastrointestinal tract, the chelates of the present invention have a good stability as well as surprising relaxivity values in human serum.

More particularly, the invention relates to compounds of formula (I), both in the racemic and optically active forms:

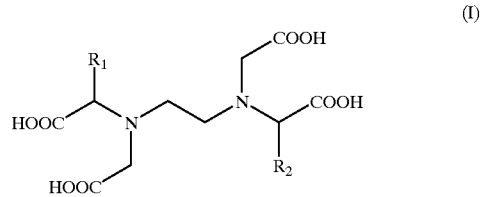

wherein:
  $R_1$, $R_2$ are independently a hydrogen atom, or a straight or branched ($C_1$–$C_{20}$) alkyl chain, saturated or unsaturated, being said chain optionally interrupted by one or, more nitrogen or sulfur atoms, as well as by —CO—, —CONH—, —NHCO—, —SO—, —$SO_2$—, —$SO_2NH$— groups, or optionally substituted by one or more $NH_2$, OH, halogen, COOH groups and the respective ester or amide derivatives, said chain being in any case interrupted or substituted by one or more $R_3$ cyclic residues, which are the same or different, non-fused or fused, with the proviso that, when some of the $R_3$ residues are fused together, the maximum number of rings forming the corresponding polycyclic unit is three, wherein
    $R_3$ is a 5- or 6-membered cyclic unit, carbocyclic or heterocyclic, saturated, unsaturated or aromatic, being said cyclic units unsubstituted or substituted with one or more $R_4$ groups, which are the same or different, wherein $R_4$ is OH, halogen, $NHR_5$, $N(R_5)_2$, $-O-R_5$, $-S-R_5$, or $-CO-R_{51}$ wherein the $R_5$ groups, which are the same or different, are a straight or branched ($C_1-C_5$) alkyl, unsubstituted or substituted with one or more hydroxy and/or alkoxy and/or carboxy groups, or $R_4$ is a COOH group, or an ester or amido derivative thereof, or a $-SO_3H$ group or an amido derivative thereof, or $R_4$ is a $-O-R_6$ group, wherein $R_6$ is a 5- or 6-membered cyclic unit, carbocyclic or heterocyclic, saturated, unsaturated or aromatic, being said cyclic unit optionally substituted by one or more OH, halogen, $-NHR_5$, $-N(R_5)_2$, $-O-R_5$, $-S-R_5$, $-CO-R_5$ groups, wherein $R_5$ has the meanings defined above, or by one or more $-COOH$ groups, or the ester or amido derivatives thereof, or $-SO_3H$ or amido derivatives thereof, with the proviso that $R_1$ and $R_2$ are not at the same time hydrogen;

as well as the chelates thereof with the manganese ion in the oxidation state +2 (Mn(II)) and the salts thereof with physiologically compatible organic bases selected from primary, secondary, tertiary amines or basic amino acids, or with inorganic bases whose cations are sodium, potassium, magnesium, calcium, or mixtures thereof.

In case the chelated complex has a total charge, this is preferably neutralized with a physiologically compatible counter-ion. Suitable substances for salifying the compounds of the invention and/or the chelates thereof, are, for example:

cations of inorganic bases such as alkali or alkaline-earth metals ions selected from sodium, potassium, magnesium, calcium, or mixtures thereof;

cations of physiologically compatible organic bases selected from primary, secondary and tertiary amines such as ethanolamine, diethanolamine, morpholine, glucamine, N-methylglucamine, N,N-dimethylglucamine;

cations of amino acids such as those of lysine, arginine or ornithine.

Particularly preferred are N-methylglucamine salts.

In the compounds of formula (I), particularly preferred meanings for $R_1$ and $R_2$ are the following:

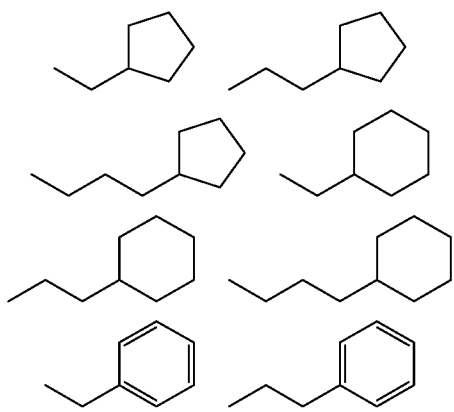

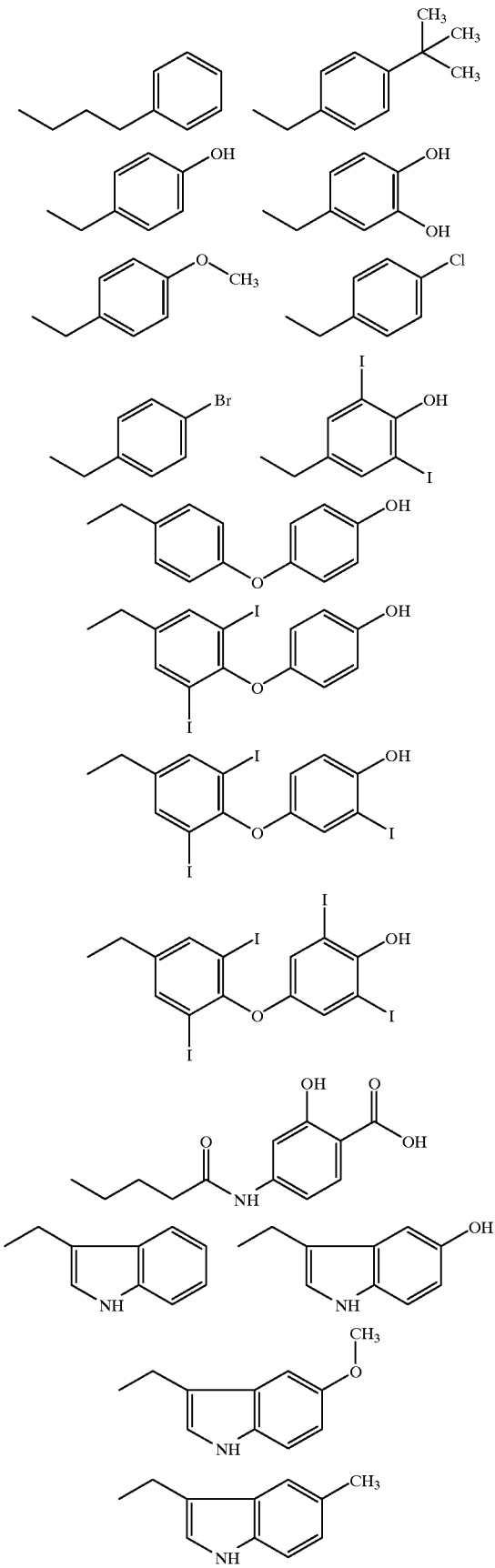

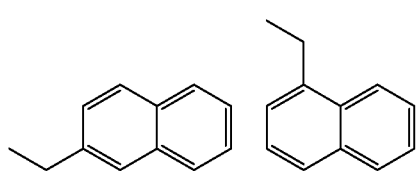
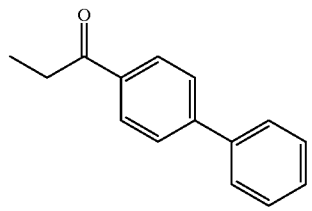
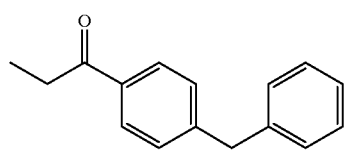
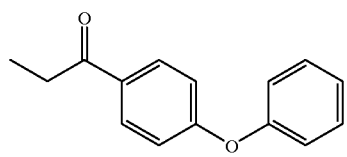
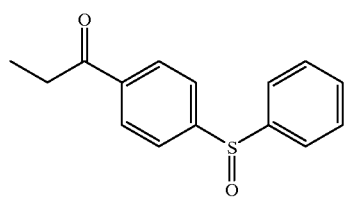
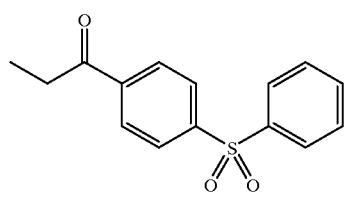
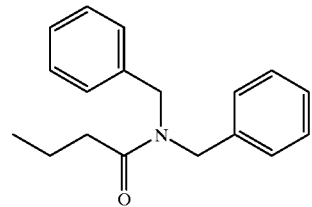
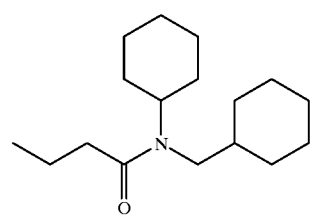
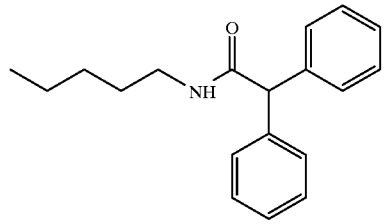
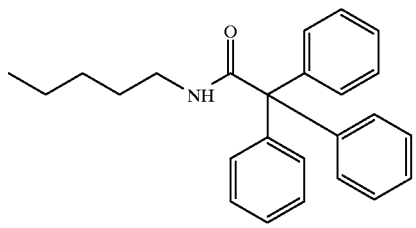
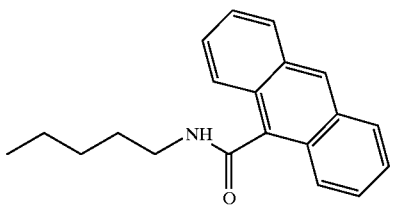
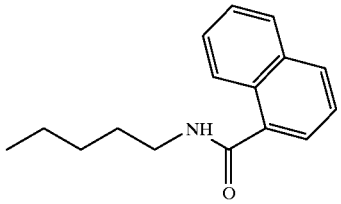
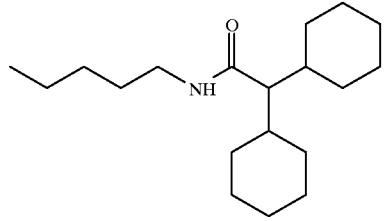
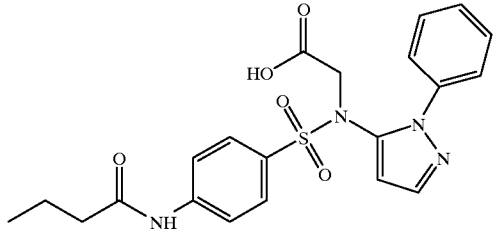
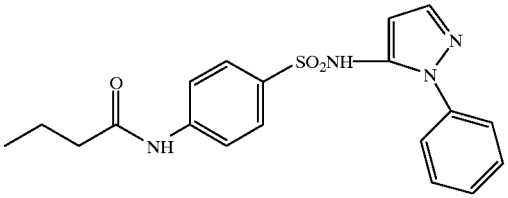
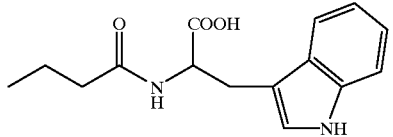

-continued

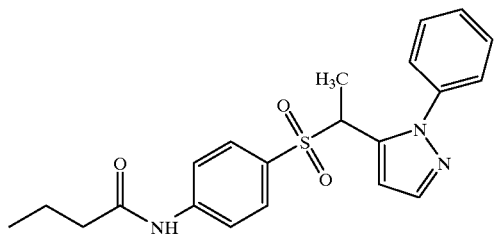

Particularly preferred classes of compounds within formula (I), are those of formula (II):

(II)

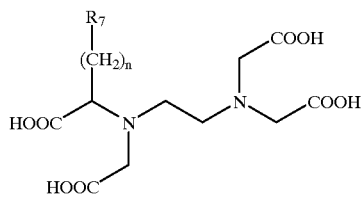

and of formula (III):

(III)

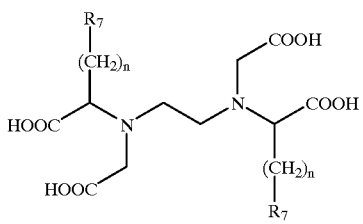

wherein:

R$_7$ is a 5- or 6-membered cyclic unit, carbocyclic or heterocyclic, saturated, unsaturated or aromatic, optionally substituted by one or more groups selected from OH, halogen, COOH or an ester or amido derivative thereof, —SO$_3$H or an amido derivative thereof, or —R$_5$, —NHR$_5$, —N(R$_5$)$_2$, —O—R$_5$, —S—R$_5$, wherein R$_5$ has the meanings defined above, or from a group selected from —O—R$_8$ and —CH$_2$R$_8$ wherein R$_8$ is a further 5- or 6-membered cyclic unit, carbocyclic or heterocyclic, saturated, unsaturated or aromatic, optionally substituted by one or more groups selected from OH, COOH and halogen;
n=1–6.

Particularly preferred classes of compounds within formula (I), are also those of formula (IV)

(IV)

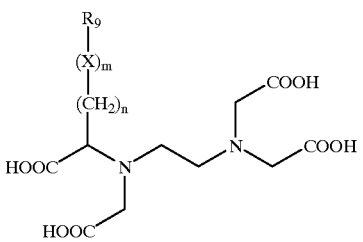

and of formula (V), respectively, (V)

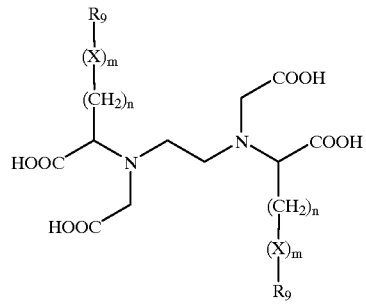

in which:

R$_9$ is a group comprising 2 or 3 cyclic units, nonfused or fused, which are the same or different, wherein said units can be carbocyclic, heterocyclic, saturated, unsaturated or aromatic;

n=1–6;

m=0 or 1;

X=—NHCO, —CONH, —CONH—CH$_2$—.

Furthermore, within formulae (II) and (III), particularly preferred compounds are those in which R$_7$ is cyclohexyl, phenyl, hydroxyphenyl or a 3,5-diiodothyronine residue; within formulae (IV) and (V), particularly preferred compounds are those in which R$_9$ is naphthalene, anthracene or indole and X is —NHCO.

Among the possible manganese chelates included within formula (I), most preferred are those having as ligands the compounds shown hereinbelow:

COMPOUND 1 (EXAMPLE 1)

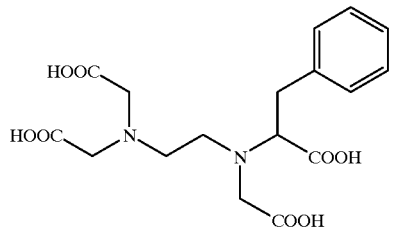

COMPOUND 2 (EXAMPLE 2)

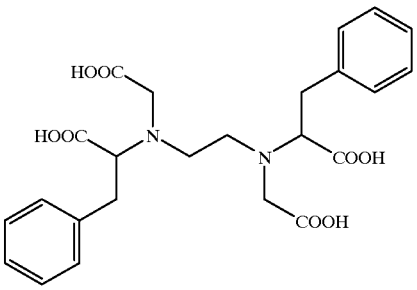

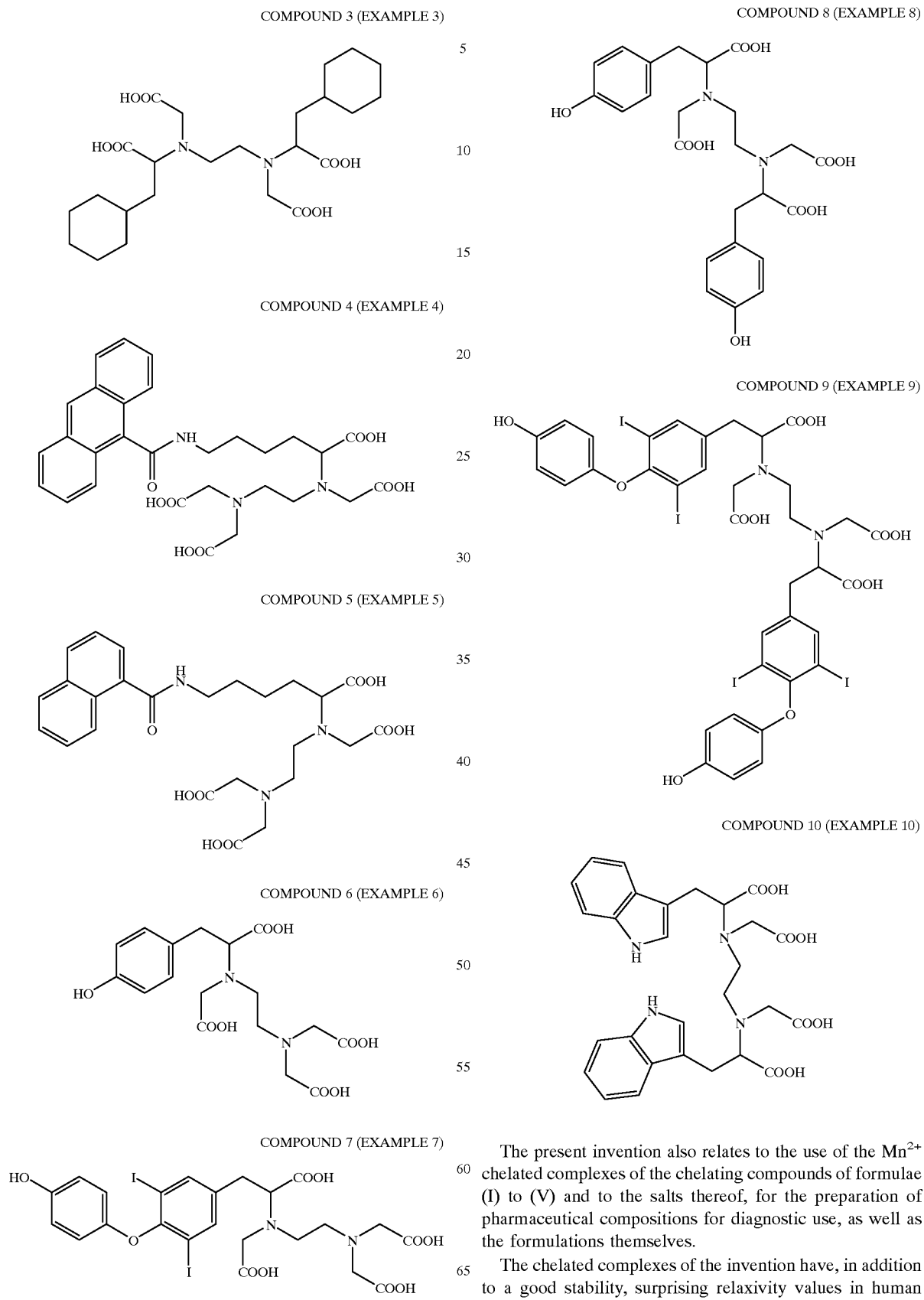

The present invention also relates to the use of the $Mn^{2+}$ chelated complexes of the chelating compounds of formulae (I) to (V) and to the salts thereof, for the preparation of pharmaceutical compositions for diagnostic use, as well as the formulations themselves.

The chelated complexes of the invention have, in addition to a good stability, surprising relaxivity values in human serum. These characteristics allow to foresee interesting applicative uses thereof, in view of an improvement in the images obtainable using said compounds in the preparation of M.R.I. contrast agents for general use, as well as the possible use thereof in specific formulations for the imaging of the cardiocirculatory system.

More particularly, the chelates of the present invention are characterized in having particularly high $r_2$ values in human serum. This makes them most suitable, and this is a further aspect of the present invention, for use in M.R.I. diagnostic imaging in recording images of organs or tissues, wherein said images are acquired by $T_2$ weighed sequences. Furthermore, the considerable increase in relaxivity in human serum shown by the compounds of the invention allows the use thereof in diagnostic formulations requiring a low dosage of the contrast agent, said formulations providing good quality images, while assuring a significant improvement from the toxicologic point of view.

The contrastographic formulations containing the chelates of the invention can therefore be formulated with concentrations of contrast agent ranging from 0.001 to 1.0 mmol/mL, preferably from 0.01 to 0.5 mmol/mL; in particular, concentrations lower than 0.25 mmol/mL for the low-dosage formulations.

Said formulations can be administered to the patient in doses ranging from 0.001 to 0.1 mmol/kg, preferably 0.1 mmol/kg; in particular, doses ranging from 5 to 50 µmol/kg when administered in low dosages.

According to the present invention, said chelated complexes proved to be particularly suitable also in the preparation of pharmaceutical formulations for M.R.I. diagnostic imaging at low fields, i.e. fields ranging from 0.1 to 0.5 Tesla or, when measuring the intensity of the applied magnetic field in Hertz, fields below 20 MHz (An introduction to Magnetic Resonance in Medicine, Ed. Peter A. Rinck). The compounds of the invention, thanks to their excellent relaxivity shown even at such low fields, can advantageously be used with apparatuses such as Artroscan (arthrographs which make use of the Magnetic resonance), open apparatuses, apparatuses intended for diagnostic of single regions of the human body (e.g. the shoulder), and generally apparatuses less expensive, easier to handle and increasingly diffused.

The chelates of the invention have also shown a good applicability in the imaging of the liver and of the biliary tracts, which organs are reached by said chelates, thus confirming their characteristics of stability.

Among the possible synthetic routes which can be used for the preparation of the compounds of the invention, those illustrated in the general schemes reported in the following are preferred.

When only one of $R_1$ or $R_2$ is different from hydrogen, a possible process is illustrated in the following Scheme 1:

SCHEME 1

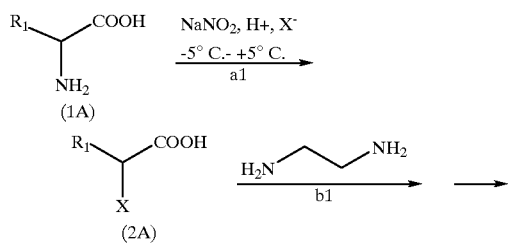

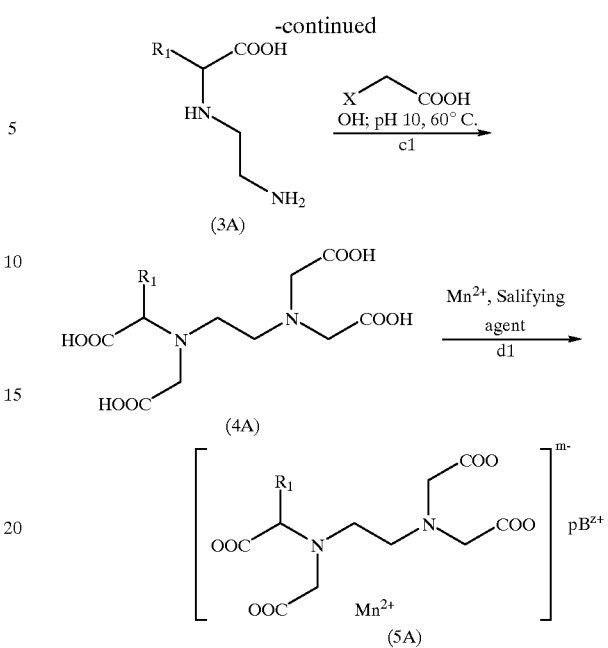

wherein:

$R_1$ has the same meanings as in formula (I);
X=halogen (Cl, Br, I);
m=number of the total charges of the chelated complex;
B=substance suitable for salifying the chelated complex (for example Na$^+$, K$^+$, Mg$^{++}$, Ca$^{++}$ or mixtures thereof, meglumine, etc.);
z=number of the charges of B;
p is an integer such that the product: p·z=m.

In step (a1) an α-amino acid (1A), natural or synthetic, is reacted with a suitable halide (e.g. KBr) in acid aqueous medium, in the presence of NaNO$_2$ and at a temperature which can range from −5 to +5° C. The resulting α-haloacid (2A) is reacted, in step (b1), with 1,2-diaminoethane in aqueous solution, at a temperature from 20 to 40° C. The resulting intermediate (3A) is carboxymethylated in step (c1), in basic medium at pH 10 with an α-haloacetic acid (e.g. bromoacetic acid) at about 60° C., to give the free ligand (4A). The latter is reacted in step (d1) with the stoichiometric amount of manganese, as salt, in the presence of the base amount necessary for the neutralization; the reaction is preferably carried out in water or in a suitable water-alcohol mixture, at 25 to 40° C.; thereby obtaining the desired chelated complex (5A).

When both $R_1$ and $R_2$ are different from hydrogen and $R_1$ is the same as $R_2$, the procedure summarized in the following Scheme 2 will be followed:

SCHEME 2

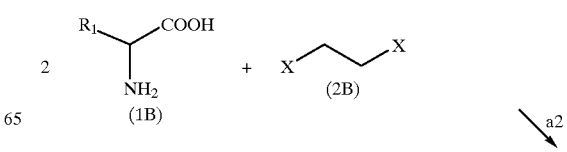

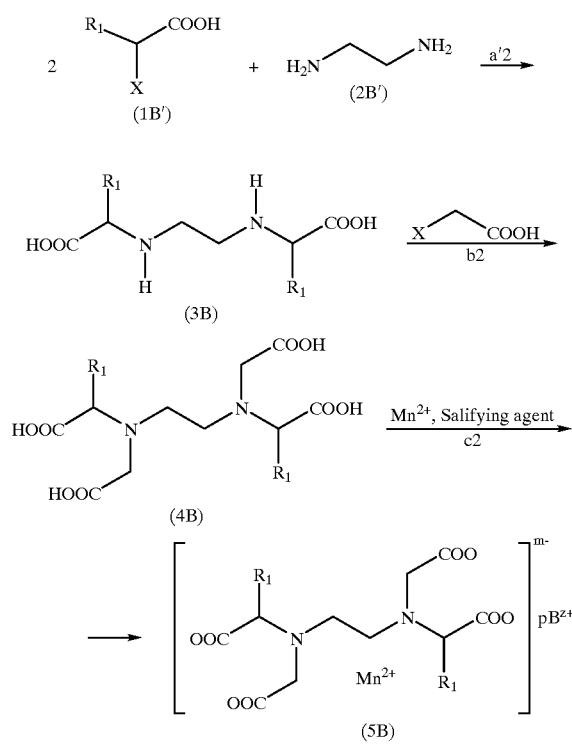

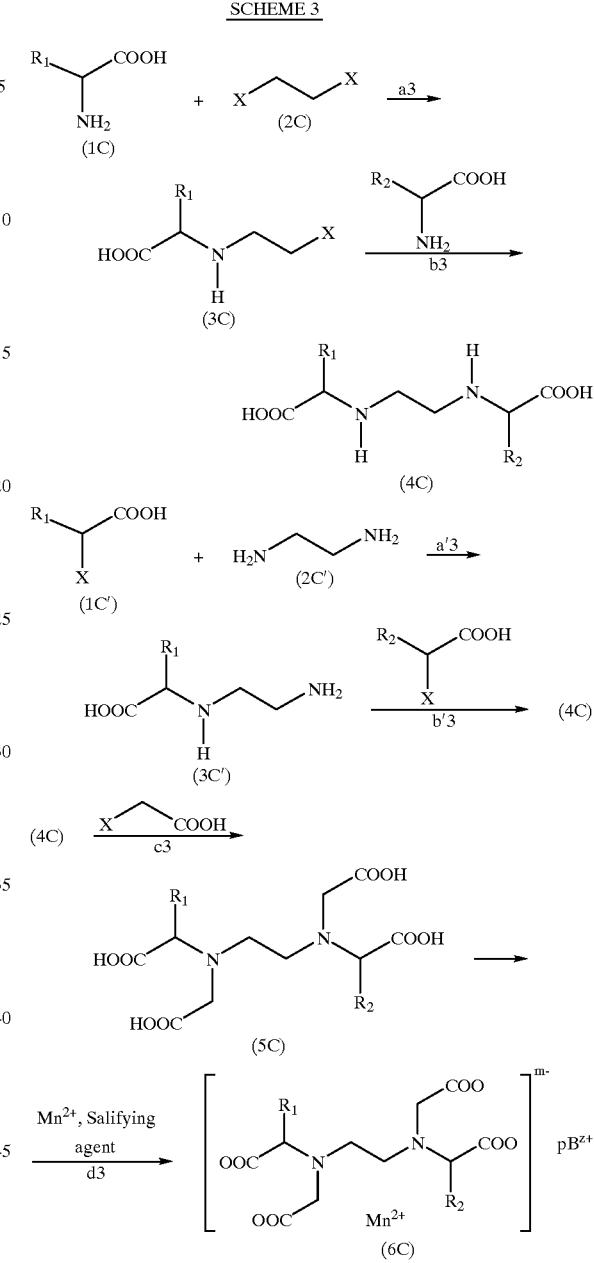

SCHEME 3 wherein:

$R_1$ has the same meanings as in formula (I);

X=halogen (Cl, Br, I);

m=number of the total charges of the chelated complex;

B=substance suitable for salifying the chelated complex (for example $Na^+$, $K^+$, $Mg^{++}$, $Ca^{++}$ or mixtures thereof, meglumine, etc.);

z=number of the charges of B;

p is such an integer that the product: p·z=m.

In step (a2), a suitable α-amino acid (1B) is reacted with a 1,2-dihaloethane, such as 1,2-dibromoethane (2B) in a suitable solvent (e.g. water/ethanol, water/methanol mixtures), keeping pH at about 9 with a suitable buffer (preferably 2M borate buffer) at a temperature which can range from 60 to 90° C. Alternatively, (step a'2), an α-haloacid (1B') can be reacted with 1,2-diaminoethane (2B') in aqueous solution at 20 to 60° C. The resulting intermediate (3B) is carboxymethylated in step (b2) with an α-haloacetic acid (e.g. bromoacetic acid) at basic pH (about 10) and at a temperature from 40 to 70° C., to give the free ligand (4B). This is reacted in step (c2) with the stoichiometric amount of manganese, according to the general procedure already described for scheme 1, to obtain the desired chelated complex (5B).

Using a different stoichiometry, asymmetric ligands can be prepared, wherein $R_1$ and $R_2$ are both different from hydrogen and different from each other, as represented in the following Scheme 3:

wherein:

$R_1$, $R_2$ have the same meanings as in formula (I);

X=halogen (Cl, Br, I);

m=number of the total charges of the chelated complex;

B=substance suitable for salifying the chelated complex (for example $Na^+$, $K^+$, $Mg^{++}$, $Ca^{++}$ or mixtures thereof, meglumine, etc.);

z=number of the charges of B;

p is an integer such that the product: p·z.=m.

An alternative process which provides disubstituted compounds is represented by the following Schemes 4A and 4B:

SCHEME 4A

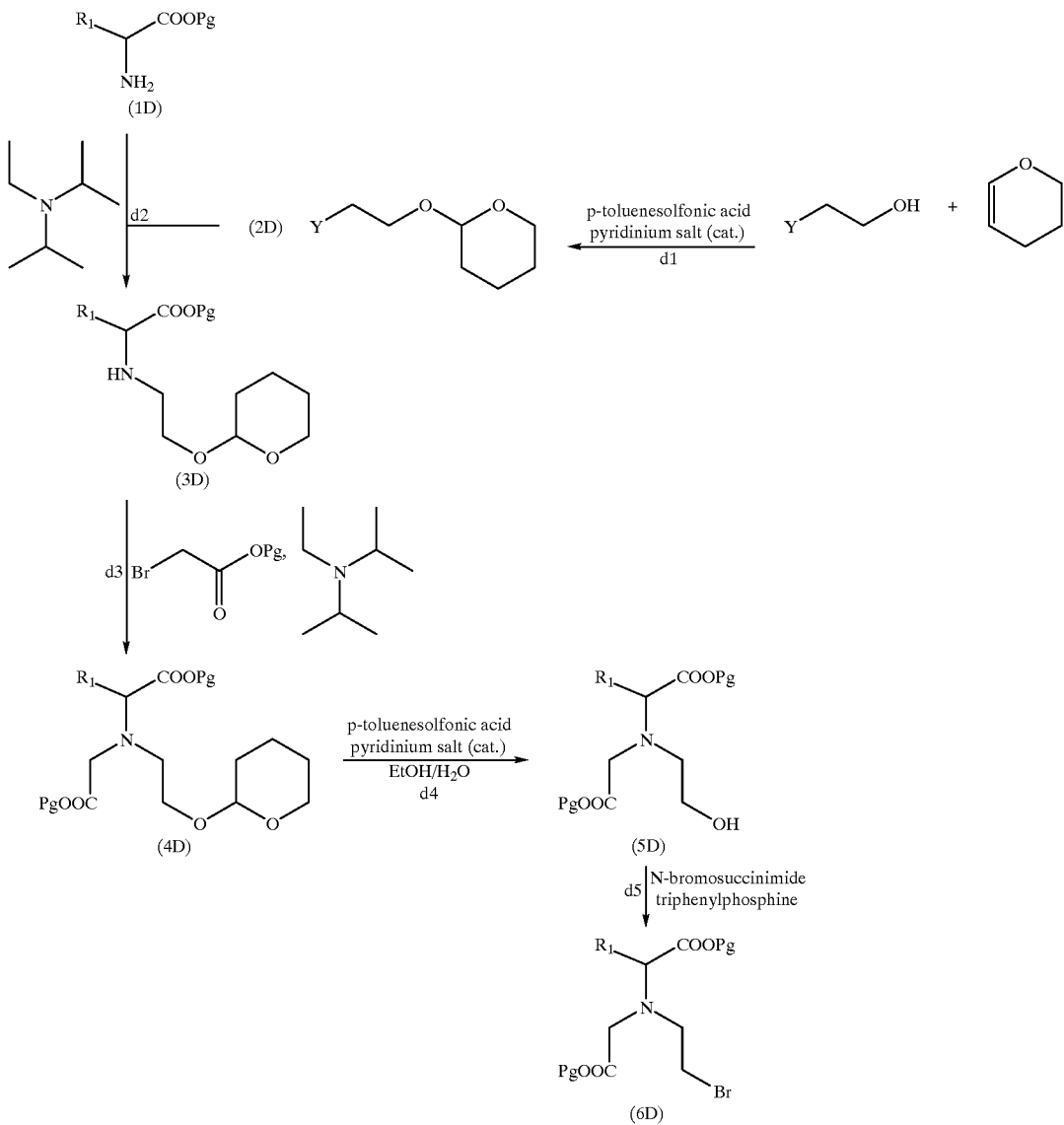

wherein:
  R$_1$ has the same meanings as in formula (I);
  Pg=protective group (e.g. t-butyl)
  Y=Cl, Br or other leaving groups (I, —OMs, —OTf, —OTs);

Step (d1) comprises the protection of the alcoholic fraction of a 2-haloethanol (preferably 2-bromoethanol) with dihydropyran, to give intermediate (2D). The alcohol-protecting group can be, for example, benzyl or trityl. The reaction takes place in an organic solvent such as CH$_2$Cl$_2$, CHCl$_3$, CH$_2$ClCH$_2$Cl, in the presence of 4-toluenesulfonic acid pyridinium salt or of another acid catalyst. In intermediate (2D), the leaving group is preferably Br.

In step (d2) the ester (e.g. t-butyl ester) of a natural or synthetic α-amino acid (1D), either in the racemic or optically active form, is reacted with the intermediate (2D) in the presence of a base, such as diisopropylethylamine, in a solvent such as CH$_3$CN, DMF or a chlorinated solvent, to give intermediate (3D).

The latter is reacted, in step (d3), with a bromoacetic acid ester (e.g. t-butyl-bromoacetate) in the presence of a base, such as diisopropylethylamine, to give intermediate (4D) which is reacted, in the subsequent step (d4), with 4-toluenesulfonic acid pyridinium salt or another acid catalyst, in an ethanol/water mixture, at a temperature of 20–60° C., to give intermediate (5D).

In step (d5), intermediate (5D) is brominated with N-bromosuccinimide in the presence of triphenylphosphine, to give intermediate (6D), which is reacted, in step (d6), with the ester (e.g. t-butyl ester) of an α-amino acid (7D), in a suitable solvent (e.g. CH$_3$CN/buffer phosphate pH 8), to give intermediate (8D). This is then reacted with a bromoacetic acid ester (e.g. t-butyl-bromoacetate) in the presence of a base, such as diisopropylethylamine, to give tetraester (9D). The latter is deprotected in step (d8) with known methods (e.g. hydrolysis with CF$_3$COOH or (CH$_3$)$_3$SiI, when the protective group is t-butyl) to give the free ligand (10D), which is subsequently complexed and salified according to the general procedure already described in the above schemes.

SCHEME 4B

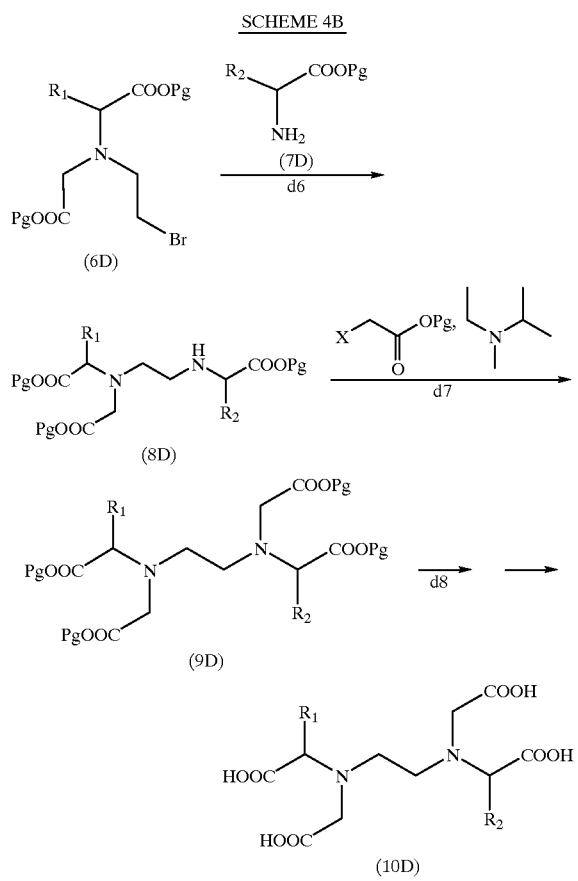

wherein:

R₁, R₂ have the same meanings as in formula (I);
Pg=protective group (e.g. t-butyl);
X=halogen (Cl, Br, I).

The following examples illustrate the best experimental conditions to prepare the compounds of the invention.

EXAMPLE 1

Manganese complex of N-[2-[bis(carboxymethyl)-amino]ethyl]-N-(carboxymethyl)-D-phenylalanine salified with 1-deoxy-1-(methylamino)-D-glucitol (1:2)

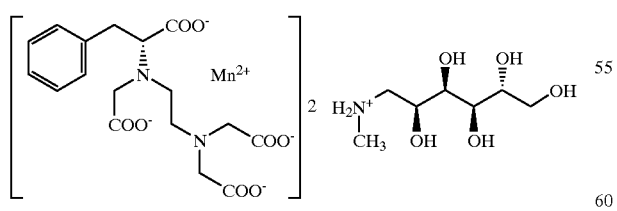

A) (S)-(α)-Bromobenzenepropanoic acid (C.A.S. [35016-63-8])

The compound was prepared according to Briggs, M. T.; Morley, J. S., J. Chem. Soc., Perkin Trans. 1979, 1(9) 2138–2143.

B) N-(2-Aminoethyl)-D-phenylalanine bis-hydrochloride

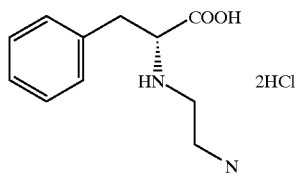

The compound from the previous step (26.17 g; 0.114 mol) was dropped, during 40 min, into a solution of ethylenediamine (100 mL; 1.5 mol) in H$_2$O (150 mL), keeping temperature below 40° C. The solution was kept under stirring at room temperature overnight, then the ethylenediamine excess was evaporated (50° C.; 2 kPa); the residue was dissolved in H$_2$O (125 mL) and acidified (pH 0.8) with 37% aqueous HCl (48 mL). The suspension was filtered, the mother solution concentrated and decolourized with Carbopuron$^{(R)}$ 4 N. After filtration, the pH of the solution was adjusted to 3 with 2N NaOH (37 mL), to obtain a precipitate which was filtered. By concentration of the mother liquors to 125 mL, a second crop of precipitate was obtained. The two precipitates were dissolved in H$_2$O (300 mL), and percolated on a column of Amberlite$^{(R)}$ IRA-400 resin (350 mL; form OH⁻), which was washed to neutrality with H$_2$O. After elution of the column with aqueous HCl, the acid eluate was evaporated and the residue was dried (P$_2$O$_5$; 2 kPa) to obtain the desired compound (15.2 g; 0.054 mol). Yield 51%.

m.p.: 230° C. dec.; Acidic titer (0.1 M NaOH): 100.9%; Argentometric titer (0.1 M AgNO$_3$): 100%; HPLC: 100% (% area).

The $^{13}$C-NMR (D$_2$O), MS and IR spectra are consistent with the indicated structure.

| $[\alpha]_\lambda^{20}$ (c 2, H$_2$O) | λ (nm) | 589 | 436 |
|---|---|---|---|
| | $[\alpha]_\lambda^{20}$ | -8.73° | -25.15° |

Elementary analysis (%):

| | C | H | N | Cl | H$_2$O |
|---|---|---|---|---|---|
| Calculated | 46.99 | 6.45 | 9.96 | 25.22 | |
| Found | 46.76 | 6.65 | 9.93 | 24.82 | <0.1 |

C) N-[2-[Bis (carboxymethyl)amino]ethyl]-N-(carboxyme-thyl)-D-phenylalanine

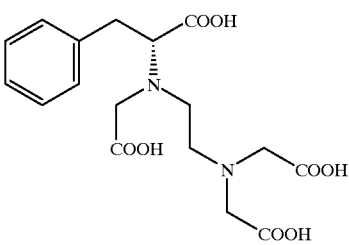

A bromoacetic acid solution (11.29 g; 0.081 mol) in H$_2$O (50 mL), was added with 10 M NaOH (8.0 mL; 0.080 mol), at 5° C., to pH 5. N-(2-Aminoethyl)-D-phenylalanine bis-hydrochloride (5.65 g; 0.020 mol) from the previous step, was dropped in the solution in 10 minutes; the reaction mixture was kept at 60° C. and pH 10 by addition of 10 M NaOH (12.1 mL; 0.121 mol) during 28 h. The reaction mixture was neutralized with 12 M HCl and percolated on a column of Amberlite(R) XAD 1600 resin (300 mL), eluting with water. The first eluate (900 mL) contained the ligand with a 90% purity (area). The aqueous solution was concentrated and acidified to pH 1.8 with 12 M HCl and percolated on a second column of resin Amberlite(R) XAD 1600 (450 mL), which was eluted with water. The first eluate (1 L) was discarded, whereas the subsequent 2 L were evaporated to dryness, to obtain the desired product (3.4 g; 0.0089 mol). Yield 44%.

m.p.: 120° C.; Acidic titer (0.1 M NaOH): 101 %; Complexometric titer (0.1 M $ZnSO_4$): 96.8%; HPLC: 98% (% area).

The $^{13}$C-NMR, $^1$H-NMR and MS spectra are consistent with the indicated structure.

| $[\alpha]_\lambda^{20}$ :(c 1, MeOH) | λ (nm) | 589 | 436 |
|---|---|---|---|
| | $[\alpha]_\lambda^{20}$ | -33.5° | -65.6° |

Elementary analysis (%):

| | C | H | N | Br | Cl | Na |
|---|---|---|---|---|---|---|
| Calculated | 53.40 | 5.80 | 7.32 | | | |
| Found on the anhydrous | 53.67 | 5.75 | 7.34 | <0.1 | <0.1 | <0.18 |

D) Manganese complex of N-[2-[bis(carboxymethyl)-amino]ethyl]-N-(carboxymethyl)-D-phenylalanine salified with 1-deoxy-1-(methylamino)-D-glucitol (1:2)

The free ligand from the previous step (2.82 g; 0.0072 mol) was suspended in $H_2O$ (20 mL) and solubilised with 1-deoxy-1-(methylamino)-D-glucitol 1 M (18.64 mL; 0.0186 mol) at pH 6.5. Afterwards, an aqueous solution 1.009 M of $MnCl_2$ (7.13 mL; 0.0072 mol) was added during 4 h, keeping pH 6.8 by addition of 1-deoxy-1-(methylamino)-D-glucitol 1 M (7.13 mL; 0.0071 mol). After 24 h the solution was filtered through Millipore(R) (HA-0.22 μ), then nanofiltered and finally concentrated to 30 mL After adjusting pH from 5.8 to 7.0 with 1-deoxy-1-(methylamino)-D-glucitol 1 M (0.3 mL), the solution was evaporated and the residue dried ($P_2O_5$; 2 kPa) to give the desired product (5.65 g; 0.0068 mol). Yield 95%.

m.p.: 110° C.; HPLC: 98.4% (% area).

The MS and IR spectra are consistent with the indicated structure.

Elementary analysis (%):

| | C | H | Mn | N | Cl |
|---|---|---|---|---|---|
| Calculated | 45.09 | 6.59 | 6.65 | 6.78 | |
| Found anhydrous | 45.47 | 6.52 | 6.39 | 6.76 | <0.1 on the |

EXAMPLE 2

Manganese complex of [N,N'-1,2-ethanediylbis [N-(carboxymethyl)-L-phenylalanine]] salified with 1-deoxy-1-(methylamino)-D-glucitol (1:2)

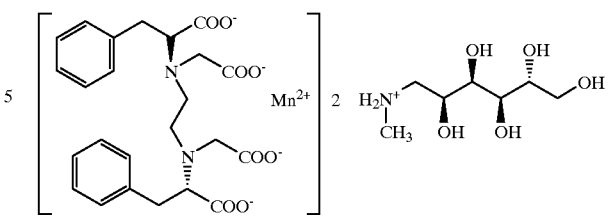

A) N,N'-1,2-Ethanediylbis-L-phenylalanine (C.A.S. [119590-67-91])

A solution of 1,2-dibromoethane (28.36 g; 0.151 mol) in EtOH (100 mL) was dropped, in 2.5 hours, in a solution of L-phenylalanine (33.51 g; 0.203 mol) in 2 M borate buffer at pH 9 (420 mL) under stirring at 90° C. At the end of the addition the reaction mixture was heated at 90° C. for 4.5 hours, then cooled to room temperature. The crystalline solid was filtered, washed with $H_2O$ and dried to obtain the desired product (21.42 g; 0.06 mol). Yield 59%.

m.p. 260° C. dec.; Acidic titer: 104.4%; HPLC: 100% (% area).

The $^1$H-NMR, $^{13}$C-NMR, MS and IR spectra are consistent with the indicated structure.

| [α]$^{20}$ (c 1,5; NaOH 0,1M) | | |
|---|---|---|
| λ (nm) | 589 | 436 |
| [α]$^{20}$ | +40.92° | +93.78° |

Elementary analysis (%):

| | C | H | N |
|---|---|---|---|
| Calculated | 67.40 | 6.79 | 7.86 |
| Found | 67.22 | 6.83 | 7.81 |

B) N,N'-1,2-EthanediylbistN-(carboxymethyl)-L-phenylalanine]

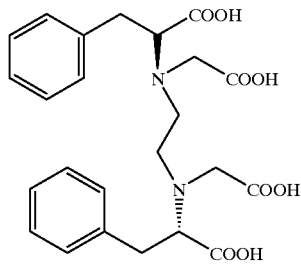

The compound from the previous atep (31 g; 0.087 mol) and bromoacetic acid (48.4 g; 0.348 mol) were dissolved at room temperature in 2N NaOH (261 mL; 0.522 mol); the reaction mixture was then heated to 50° C., keeping pH 10.5 by addition of 2N NaOH (156 ML; 0.312 mol) during 24 h. The solution was extracted with n-BuOH (200 mL+2×100 mL) saturated with water. The aqueous phase was concentrated to 75 mL and dropped in 1.75 M HCl (250 mL). pH was adjusted to 1.7 with 2 N NaOH (3.5 mL). After 18 h the precipitate was filtered, suspended in H₂O (80 mL) and dissolved with 10 N NaOH (15.55 mL) to pH 4.6. EtOH (1000 mL) was added to obtain a precipitate of the disodium salt of the desired product, which was filtered and dissolved in H₂O (150 mL). The solution was dropped in 0.25 M HCl (610 mL), the precipitate was filtered, washed with H₂O and dried (P₂O₅; 2 kPa), to give the desired product (17.2 g; 0.036 mol). Yield 42%.

m.p.: 148–151° C. dec.; Acidic titer (0.1 M NaOH): 99%; Complexometric titer (0.1 M ZnSO₄): 97.7%; HPLC: 100% (% area).

The $^{13}$C-NMR, $^{1}$H-NMR, IR and MS spectra are consistent with the indicated structure.

| Elementary analysis (%): | | | | |
|---|---|---|---|---|
| | C | H | Mn | N |
| Calculated | 49.83 | 6.60 | 5.99 | 6.12 |
| Found at 90° C. | 49.81 | 6.53 | 6.05 | 6.16 after drying |

EXAMPLE 3

Manganese complex of [[S—(R*,R*)]-α,α'-[1,2-ethane-diyl-bis[(carboxymethyl)imino]]bis(cyclohexanepropanoic) acid salified with 1-deoxy-1-(methylamino)-D-glucitol (1:2)

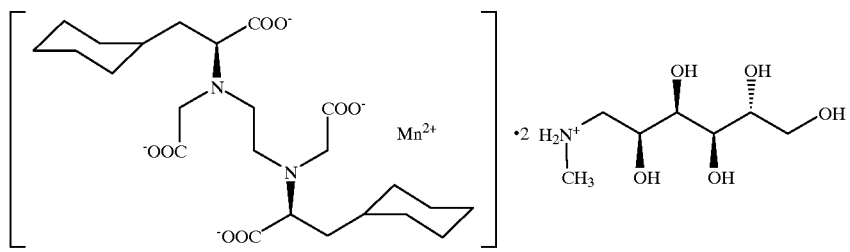

| | $[\alpha]^{20}_\lambda$:(c 1,5; NaOH 0,1M) | |
|---|---|---|
| λ(nm) | 589 | 436 |
| $[\alpha]^{20}_\lambda$ | +13.04° | +30.05° |

| Elementary analysis (%): | | | |
|---|---|---|---|
| | C | H | N |
| Calculated | 61.01 | 5.97 | 5.93 |
| Found | 60.91 | 5.93 | 5.91 on the anhydrous |

C) Manganese complex of (N,N'-1,2-ethanediylbis[N-(carboxy-methyl)-L-phenylalanine]] salified with 1-deoxy-1-(methylamino)-D-glucitol (1:2)

The free ligand from the previous sted (7.45 g; 0.0158 mol) was suspended in H₂O (35 mL) and solubilised with 1 M 1-deoxy-1-(methylamino)-D-glucitol (24 mL; 0.024 mol) at pH 3.4. Afterwards, an aqueous solution of 0.964 M MnCl₂ (15.56 mL; 0.015 mol) was added in one hour, keeping pH 6 by addition of 1-deoxy-1-(methylamino)-D-glucitol 1 M (35.6 mL; 0.0356 mol). After 24 h (pH 6.5) the solution was filtered through a Millipore$^{(R)}$ HA 0.45 μm filter, diluted with H₂O, nanofiltered and then concentrated to 40 mL. After adjusting pH to 6.9 with 1-deoxy-1-(methylamino)-D-glucitol 1 M (0.11 mL), the solution was evaporated and the residue dried (P₂O₅; 2 kPa) to give the desired product (14.15 g; 0.015 mol). Yield 98%.

m.p.: 105° C; HPCE: 98.7% (% area).

The MS and IR spectra are consistent with the indicated structure.

A) L-Phenylalanine 1,1-dimethylethyl ester

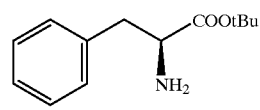

98% H₂SO₄ (7 mL; 0.13 mol) was dropped in 20 min in dioxane (70 mL), keeping temperature of the solution below 20° C. After addition of L-phenylalanine (commercial product) (16.5 g; 0.10 mol), the solution was stirred for 12 h at 132 kPa under isobutene atmosphere (commercial product) (absorbed 45 g; 0.80 mol). The solution was dropped in a mixture of ice (200 g) and 10 N NaOH (30 mL, 0.30 mol) and extracted with Et₂O (1 L). After washing with H₂O (150 mL), the organic phase was dried over Na₂SO₄ and evaporated under vacuum The residue was distilled, to obtain the desired product (13 g; 0.059 mol). Yield 59%.

b.p.: 85–90° C. at 5.3 Pa; Acidic titer (0.1 N HCl): 99.7%; HPLC: 98% (% area).

The $^{1}$H-NMR, $^{13}$C-NMR, MS and IR spectra are consistent with the indicated structure.

$[\alpha]_D^{20}$: +16,64° (c 5,29; CHCl₃)

| Elementary analysis (%): | | | |
|---|---|---|---|
| | C | H | N |
| Calculated | 70.56 | 8.65 | 6.33 |
| Found | 71.21 | 8.89 | 6.61 |

B) N-[2-(1,1-dimethylethoxy)-2-oxoethyl]-N-(2-hydroxy-ethyl)-L-phenylalanine 1,1-dimethylethyl ester

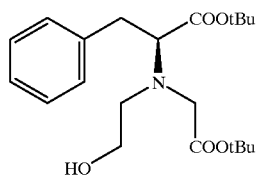

A solution of L-phenylalanine 1,1-dimethyl ester (221.3 g; 1 mol), 2-(2-bromoethoxy)tetrahydropyran, prepared according to: J. Org. Chem. 1986, 51, 752–755 (282.3 g; 1.35 mol) and diisopropylethylamine (commercial product) (175 mL; 1 mol) in $CH_3CN$ (1 L) was refluxed for 14 h. The mixture was added with diisopropylethylamine (commercial product) (175 mL; 1 mol) and tert-butylbromoacetate (commercial product) (233 g; 1.2 mol) and then refluxed for a further 2 h. The solution was evaporated, to obtain a residue which was dissolved in n-hexane (2 L) and washed with $H_2O$ (1.4 L), 1 N HCl (500 mL), 1 N NaOH (100 mL) and $H_2O$ (200 mL). The solution was evaporated and the residue was dissolved in MeOH (2 L) and added with 2 N HCl (1 L). After 2 h 2 N NaOH (1.2 L) was added, the solution was evaporated and added with n-hexane (2 L). The organic solution was evaporated to obtain the desired product (280 g; 0.738 mol). The product was used in the subsequent step without further purification. Yield 74%. HPLC: 91% (% area)
$[\alpha]_D^{20}$: –19,15° (c 5,08; $CHCl_3$)

In another preparation the compound was purified by flash chromatography (Stationary phase: silica gel 230–400 mesh Merck KGaA art. 9385. Eluent: n-hexane/EtOAc 4:1) and used for the analytical characterization.

Acidic titer (0.1 N $HClO_4$): 98.6%; HPLC: 97.4% (% area).

The $^1H$-NMR, $^{13}C$-NMR, MS and IR spectra are consistent with the indicated structure.

| Elementary analysis (%): | | | |
|---|---|---|---|
| | C | H | N |
| Calculated | 66.46 | 8.76 | 3.69 |
| Found | 66.13 | 9.32 | 3.68 |

C) N-(2-Bromoethyl)-N-[2-(1,1-dimethylethoxy)-2-oxo-ethyl]-L-phenylalanine 1,1-dimethylethyl ester

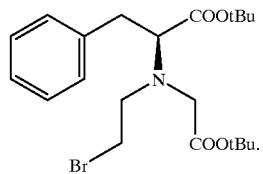

N-Bromosuccinimide (46.3 g; 0.26 mol) was added to a solution of the product from the previous step (75.9 g; 0.20 mol) and triphenylphosphine (68.1 g; 0.26 mol) in $CH_2Cl_2$ (500 mL), cooled to 0 5° C. and kept under stirring. The solution was left to stand until reaching room temperature and, after 4 h, was washed with $H_2O$ (400 mL), 5% aqueous $NaHCO_3$ (200 mL) and $H_2O$ (100 mL). After drying ($Na_2SO_4$) the solution was evaporated and the residue was suspended in $Et_2O$ (1 L); the solid (triphenylphosphine oxide) was filtered off and the solution evaporated. The residue was dissolved in n-hexane (500 mL) and added with Carbopuron$^{(R)}$4N (commercial product) (4 g), which was filtered off after a short. stirring. The solution was evaporated to a residue (77 g) which was purified by flash chromatography (stationary phase: Silica gel 230–400 mesh Merck KGaA art. 9385 (1 kg); eluent: $Et_2O$) to obtain the desired product (68 g; 0.154 mol). Yield 77%. TLC: Rf 0.46

Stationary phase: Silica gel plates 60 $F_{254}$ (Merck KGaA cod. 5715); Eluent: n-hexane/EtOAc 4:1; Detection: 1% $KMnO_4$ in 1 N NaOH; HPLC: 92% (% area).

D) (S)-N-[2-(1,1-dimethylethoxy)-2-oxoethyl]-N-[2-[[1-[(1,1-dimethylethoxy)carbonyl]-2-phenylethyl]amino] ethyl]-L-phenylalanine 1,1-dimethylethyl ester

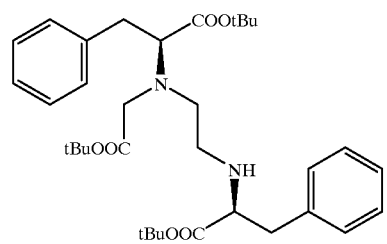

A solution of the product from the previous step (31 g; 0.067 mol) in $CH_3CN$ (50 mL) was dropped, during 3 h, in a diphasic solution of L-phenylalanine 1,1-dimethyl ester (obtained in preparation (A)) (15 g; 0.067 mol) in $CH_3CN$ (250 mL) and 2 M buffer phosphate at pH 8 (190 mL), under strong stirring at room temperature. After 20 hours the two phases were separated and the organic phase was evaporated off. The residue was dissolved in n-hexane (500 mL) and the solution was washed with $H_2O$ (2×200 mL+50 mL). The aqueous phase was in its turn washed with n-hexane (100 mL). After drying ($Na_2SO_4$), the organic phases were combined and evaporated and the residue was purified by flash chromatography (stationary phase: silica gel 230–400 mesh Merck KGaA art. 9385; h 20 cm; ¥ 11 cm. Eluent: n-hexane/EtOAc 85:15) to give the desired product (22.97 g; 0.039 mol). Yield 58%.

TLC: Rf 0.25; Stationary phase: Silica gel plates 60 $F_{254}$ (Merck KGaA Cod. 5715); Eluent: n-hexane/EtOAc 4:1; Detection: 1% $KMnO_4$ in 1 N NaOH; HPLC: 100% (% area).

The $^{13}C$-NMR, MS and IR spectra are consistent with the indicated structure.

$[\alpha]_{365}^{20}$: +12,82° (c 5, $CHCl_3$)

| Elementary analysis (%): | | | |
|---|---|---|---|
| | C | H | N |
| Calculated | 70.07 | 8.65 | 4.80 |
| Found | 70.15 | 8.86 | 5.05 |

E) N,N'-1,2-Ethanediylbis[N-[2-(1,1-dimethylethoxy)-2-oxoethyl]-L-phenylalanine 1,1-dimethylethyl ester

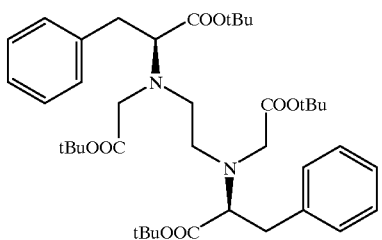

A solution of the product from the previous step (22.1 g; 0.038 mol), t-butyl bromoacetate (8.1 g; 0.042 mol) and diisopropylethylamine (8.2 mL; 0.038 mol) in $CH_3CN$ (200 mL) were left under stirring at room temperature for 40 hours, then heated to 40° C. for 20 hours. The solution was evaporated and the residue was dissolved in n-hexane (200 mL), then washed with $H_2O$ (100 mL+2×50 mL). The aqueous phase was in its turn washed with n-hexane (95 mL). The combined organic extracts were evaporated and the residue was purified by flash chromatography (Stationary phase: silica gel 230–400 mesh Merck KGaA art. 9385; h 14 cm; φ 10 cm. Eluents: n-hexane; n-hexane/EtOAc 95:5) to obtain the desired product (22.68 g; 0.032 mol). Yield 86%. TLC: Rf 0.6

Stationary phase: Silica gel plates 60 $F_{254}$ (Merck KGaA Cod. 5715); Eluent: n-hexane/EtOAc 4:1; Detection: 1% $KMnO_4$ in 1 N NaOH; HPLC: 100% (% area).

The $^{13}C$-NMR, MS and IR spectra are consistent with the indicated structure.

| | $[\alpha]_\lambda^{20}$ (c 5, $CHCl_3$): | | | | | |
|---|---|---|---|---|---|---|
| λ(nm) | 365 | 405 | 436 | 546 | 578 | 589 |
| $[\alpha]_\lambda^{20}$ | −94.26° | −68.93° | −56.04° | −32.11° | −28.15° | −26.02° |

| Elementary analysis (%): | | | |
|---|---|---|---|
| | C | H | N |
| Calculated | 68.94 | 8.68 | 4.02 |
| Found | 69.00 | 9.01 | 4.00 after drying at 80° C. |

F) [S—(R*,R*)]-α,α'-[1,2-ethanediylbis[[2-(1,1-dimethylethoxy)-2-oxoethyl]imino]]bis-(cyclohexanepropanoic)acid 1,1-dimethylethyl ester

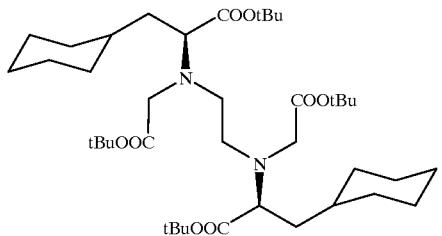

The compound from the above step (17.38 g; 0.025 mol) was dissolved in $CH_3OH$ (220 mL) and added with 5% Rh-on-charcoal. The suspension was hydrogenated in a Parr bomb (mod. 4561, 300 mL) under 40 bars (4 MPa) and 65° C. for 6 hours. The catalyst was filtered through Buchner funnel and through a Millipore FH 0.5 μm filter washing with $CH_3OH$ (50 mL). The solution was evaporated and the residue was purified by flash chromatography (Stationary phase: silica gel 230–400 mesh Merck KGaA art. 9385; h 10 cm; φ 8 cm. Eluent: n-hexane/EtOAc 95:5) to obtain the desired product (15.1 g; 0.021 mol). Yield 85%.

TLC: Rf 0.33; Stationary phase: Silica gel plates 60 $F_{254}$ (Merck KGaA Cod. 5715); Eluent: n-hexane/EtOAc 95:5; Detection: 1% $KMnO_4$ in 1 N NaOH.

The $^{13}C$-NMR, MS and IR spectra are consistent with the indicated structure.

| | $[\alpha]_\lambda^{20}$ (c 5, $CHCl_3$): | | | | | |
|---|---|---|---|---|---|---|
| λ | 365 | 405 | 436 | 546 | 578 | 589 |
| $[\alpha]_\lambda^{20}$ | −111.61° | −82.10° | −67.20° | −38.76° | −34.00° | −32.37° |

| Elementary analysis (%): | | | |
|---|---|---|---|
| | C | H | N |
| Calculated | 67.76 | 10.24 | 3.95 |
| Found | 67.97 | 10.43 | 3.86 after drying at 80° C. |

G) [S—(R*,R*)]-α,α'-[1,2-Ethanediylbis[(carboxymethyl)imino]]-bis(cyclohexanepropanoic) acid

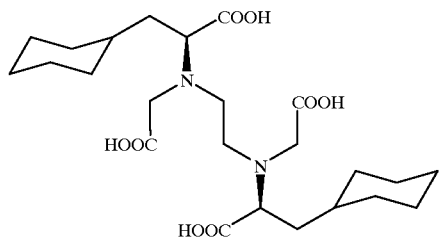

$(CH_3)_3SiI$ (30 mL; 0.22 mol) was dropped, during 50 min., in a solution of the compound from the above step (15.7 g; 0.022 mol) in $CHCl_3$ (80 mL), stirred at 5–10° C. under hydrogen atmosphere. The solution was left under stirring at room temperature for 72 hours, subsequently dropped in ice-water (125 g), then $NaHSO_3$ (0.235 g) was added to complete decolourization. The amorphous orange precipitate was solubilised at pH 8 with 10 N NaOH (26 mL), the mixture was concentrated to 100 mL and dropped in 1 N HCl (98 mL). pH was adjusted to 1 with 2 N NaOH (12 mL). After 15 hours the precipitate was filtered, washed with $H_2O$ (200 mL) and dried ($P_2O_5$; 2 kPa). The solid was dissolved in $CF_3COOH$ (80 mL) at room temperature and left under stirring for 20 hours. The solution was evaporated and the residue was suspended in $H_2O$ (150 mL), to obtain a precipitate which was filtered, washed with $H_2O$ (250 mL), suspended again in $H_2O$ (50 mL) and solubilised at pH 7.2 with 2 N NaOH (32 mL). The solution was decolourized with Carbopuron$^{(R)}$ 2S and dropped in HCl 2 N (35 mL; pH 1). The filtered solid was washed with $H_2O$ (300 mL), suspended in $H_2O$ (50 mL) and dropped in 2 N HCl (34 mL). The precipitate was filtered, washed with $H_2O$ and dried ($P_2O_5$; 2 kPa), to obtain the desired product (10.53 g; 0.021 mol). Yield 90%.

m.p.: 205° C. dec.; Acidic titer: 98%; Complexometric titer (0.1 M $ZnSO_4$): 97%; TLC: Rf 0.66; Stationary phase: Silica gel plates 60 $F_{254}$ (Merck KGaA cod. 5715); Eluent: $CHCl_3$/AcOH/$H_2O$ 5:5:1; Detection: 1% $KMnO_4$ in 1 N NaOH.

The $^1H$-NMR, $^{13}C$-NMR, MS and IR spectra are consistent with the indicated structure.

Elementary analysis (%):

|  | C | H | N |
|---|---|---|---|
| Calculated | 59.48 | 8.32 | 5.78 |
| Found | 59.96 | 8.40 | 5.58 on the anhydrous |

H) Manganese complex of [S—(R*,*)]-α,α'-[1,2-ethanediylbis[(carboxymethyl)imino]]bis(cyclohexane propanoic)acid salified with 1-deoxy-1-(methylamino)-D-glucitol (1:2)

The free ligand from the above step (8.51 g; 0.017 mol) was suspended in $H_2O$ (70 mL) and solubilised with 1-deoxy-1-(methylamino)-D-glucitol 1 M (44 mL; 0.044 mol) at pH 6. After that, an aqueous solution of 0.995 M $MnCl_2$ (17 mL; 0.017 mol) was added, during 50 minutes, keeping pH 6 by addition of 1-deoxy-1-(methylamino)-D-glucitol (67.5 mL; 0.0675 mol). After 24 hours (pH 6.5) the solution was filtered through Millipore(R) HA 0.45 μm filter, diluted with $H_2O$, nanofiltered and then concentrated to 40 mL. After adjusting pH to 6.97 with 1-deoxy-1-(methylamino)-D-glucitol 0.1 M (0.5 mL), the solution was evaporated and the residue dried ($P_2O_5$; 2 kPa) to give the desired compound (14.29 g; 0.015 mol) Yield 90%.

m.p.: 98–101%.

The MS and IR spectra are consistent with the indicated structure.

Elementary analysis (%):

|  | C | H | Mn | N |
|---|---|---|---|---|
| Calculated | 49.18 | 7.82 | 5.92 | 6.04 |
| Found | 49.44 | 7.99 | 5.93 | 6.01 on the anhydrous |

EXAMPLE 4

Manganese complex of $N^2$-[2-[bis(carboxymethyl)amino]ethyl]-$N^2$-(carboxymethyl)-$N^6$-[(9-anthracenyl)carbonyl]-L-lysine salified with 1-deoxy-1-(methylamino)-D-glucitol (1:2)

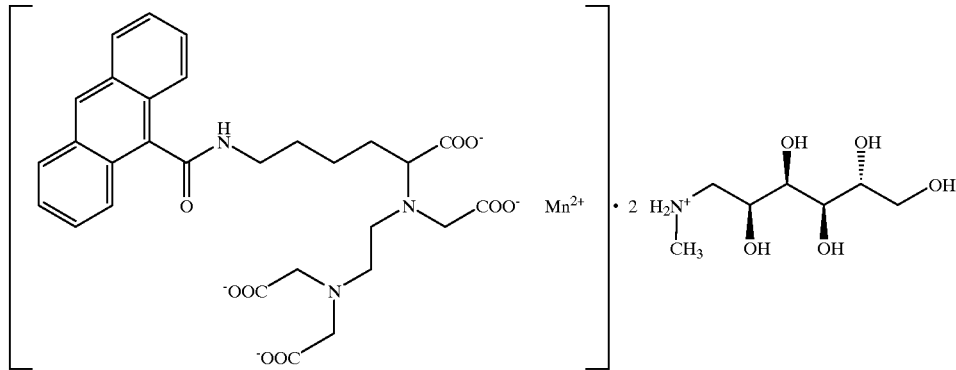

A) $N^6$-[(Phenylmethoxy)carbonyl]-L-lysine 1,1-dimethylethyl ester C.A.S. [21957-42-6]

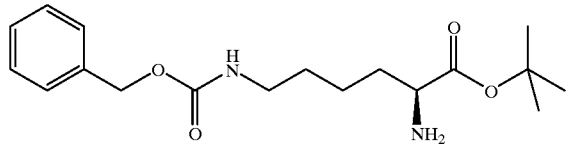

The compound was prepared according to: Bentley, P. H.; Stachulski, A. V. *J. Chem. Soc. Perkin Trans.* I, 1187–1192, 1983.

B) $N^6$-[(phenylmethoxy)carbonyl]-$N^2$-[2-[bis[2-(1,1-dimethylethoxy)-2-oxoethyl]amino]ethyl]-$N^2$-[2-(1,1-dimethylethoxy)-2-oxoethyl]-L-lysine 1,1-dimethylethyl ester

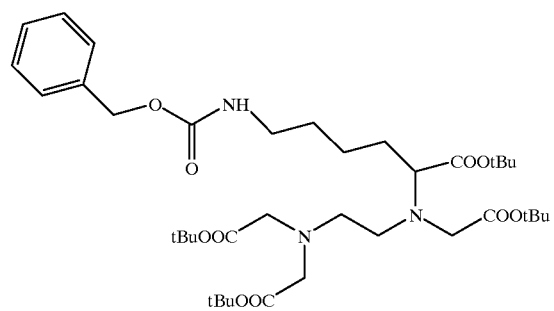

The compound was prepared according to the synthetic procedure reported in Schemes 4A and 4B of the general disclosure.

C) $N^2$-[2-[bis[2-(1,1-dimethylethoxy)-2-oxoethyl]amino]ethyl]-$N^2$-[2-(1,1-dimethylethoxy)-2-oxoethyl]-L-lysine 1,1-dimethylethyl ester

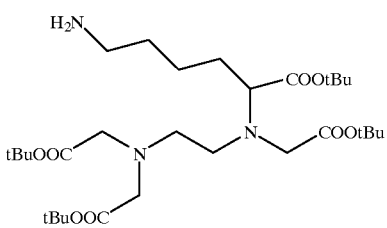

The compound was prepared from the intermediate obtained in the previous step by hydrogenation with 5% Pd/C under hydrogen atmosphere at 20° C., filtration and subsequent chromatographic purification.

D) 9-Anthracenecarboxylic acid chloride

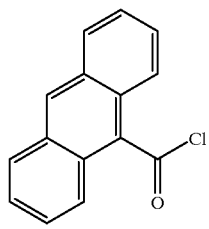

The compound was prepared from 9-anthracenecarboxylic acid (commercial product) by treatment with $SOCl_2$ according to methods known to those skilled in the art.

E) $N^2$-[2-[bis[2-(1,1-dimethylethoxy)-2-oxoethyl]amino]ethyl]-$N^2$-[2-(1,1-dimethylethoxy)-2-oxoethyl]-$N^6$-[(9-anthracenyl)carbonyl]-L-lysine 1,1-dimethyl-ethyl ester

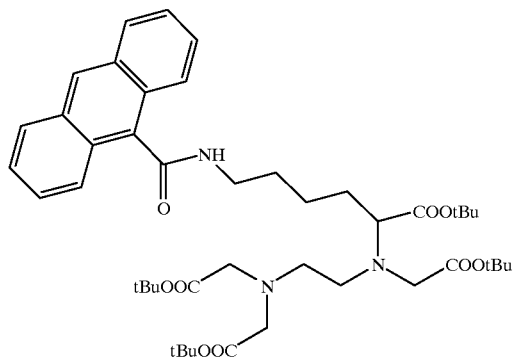

A solution of 9-anthracenecarboxylic acid chloride in $CHCl_3$ was dropped in a solution of the compound from the above step (C) in $CHCl_3$ at 5÷10° C. The resulting solution was washed with an $NaHCO_3$ aqueous saturated solution. The organic phase was dried. and concentrated to dryness, then purified by chromatography, to obtain the desired product.

F) $N^2$-[2-[bis(carboxymethyl)amino]ethyl]-$N^2$-(carboxymethyl)-$N^6$-[(9-anthracenyl)carbonyl]-L-lysine

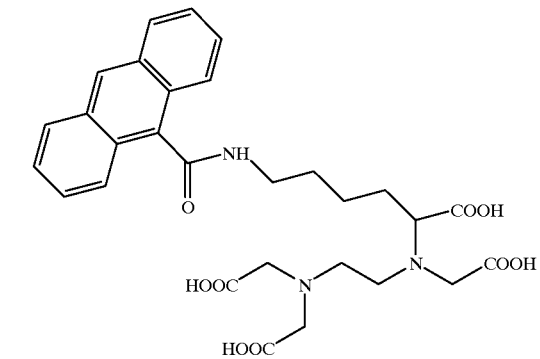

The compound was prepared from the tetraester from the previous step by hydrolysis with $CF_3COOH$ according to known methods.

G) Manganese complex of $N^2$-[2-[bis(carboxymethyl)amino]ethyl]-$N^2$-(carboxymethyl)-$N^6$-[(9-anthracenyl)carbonyl]-L-lysine salified with 1-deoxy-1-(methylamino)-D-glucitol (1:2)

The free ligand from the previous step was complexed with $MnCl_2$ and salified with 1-deoxy-1-(methylamino)-D-glucitol according to the procedure reported in Scheme 1 of the general disclosure. Yield 20% starting from step 4A.

EXAMPLE 5

Manganese complex of $N^2$-[2-[bis(carboxymethyl)amino]ethyl]-$N^2$-(carboxymethyl)-$N^6$-[(1-naphthyl)-carbonyl]-L-lysine salified with 1-deoxy-1-(methylamino)-D-glucitol (1:2)

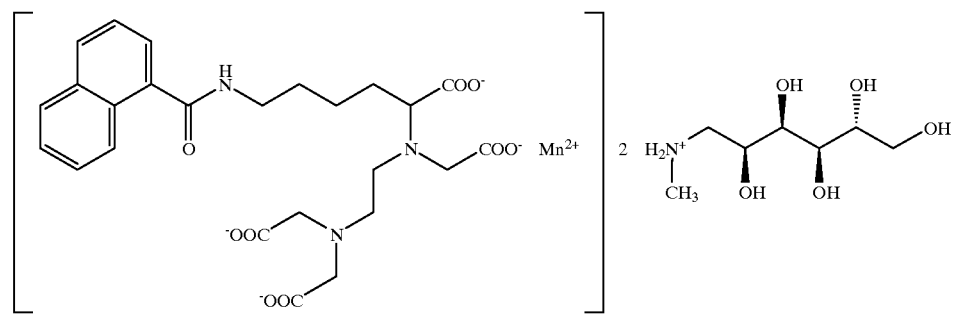

A) $N^2$-[2-[bis(carboxymethyl)amino]ethyl]-$N^2$-(carboxymethyl)-$N^6$-[(1-naphthyl)carbonyl]-L-lysine

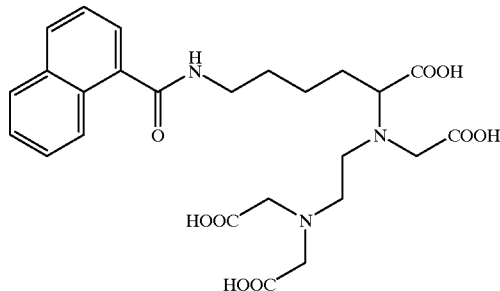

The free ligand was obtained with a process similar to that of the previous example, using in step (E) 1-naphthalenecarboxylic acid chloride (commercial product).

B) Manganese complex of $N^2$-[2-[bis(carboxymethyl)-amino]ethyl]-$N^2$-(carboxymethyl)-$N^6$-[(1-naphthyl)-carbonyl]-L-lysine salified with 1-deoxy-1-(methylamino)-D-glucitol (1:2)

The free ligand from the previous step was complexed with $MnCl_2$ and salified with 1-deoxy-1-(methylamino)-D-glucitol according to the procedure reported in Scheme 1 of the general disclosure. Yield 23% starting from step 5A.

EXAMPLE 6

Manganese complex of N-[2-[bis (carboxymethyl)amino] ethyl]-N-(carboxymethyl)-L-tyrosine salified with 1-deoxy-1-(methylamino)-D-glucitol (1:2)

A) N-[2-[bis(carboxymethyl)amino]ethyl]-N-(carboxymethyl)-L-tyrosine

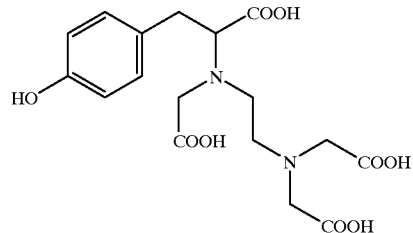

The compound was prepared according to the process reported in Schemes 4A and 4B of the general disclosure, starting from L-tyrosine 1,1-dimethylethyl ester (commercial product—CAS no. 16874-12-7).

B) Manganese complex of N-[2-[bis(carboxymethyl)amino]ethyl]-N-(carboxymethyl)-L-tyrosine salified with 1-deoxy-1-(methylamino)-D-glucitol (1:2)

The free ligand from the previous step was complexed with $MnCl_2$ and salified with 1-deoxy-1-(methylamino)-D-glucitol according to the procedure of Scheme 1 of the general disclosure. Overall yield 18%.

EXAMPLE 7

Manganese complex of N-[2-[bis(carboxymethyl)-amino]ethyl]-N-(carboxymethyl)-O-(4-hydroxyphenyl)-3,5-diiodo-L-tyrosine salified with 1-deoxy-1-(methylamino)-D-glucitol (1:2)

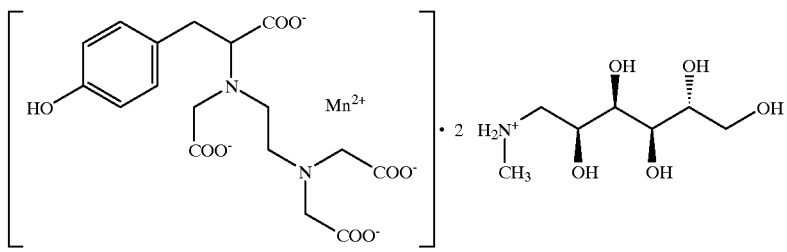

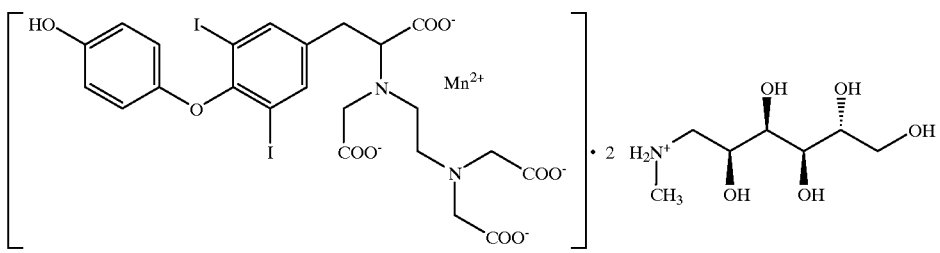

A) O-(4-hydroxyphenyl)-3,5-diiodo-L-tyrosine methyl ester

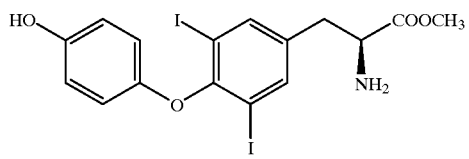

A 6 M solution of HCl in MeOH (8 mL; 48 mmol) was added to a suspension of O-(4-hydroxyphenyl)-3,5-diiodo-L-tyrosine (2.12 g; 5 mmol) (prepared according to: Chalmers J. R., Dickson G. T., Elks J. and Hems D. A., "The Synthesis of Thyroxine and Related Substances", Part V., *J. Chem. Soc.*, 3424–3433, 1949) in MeOH (12 mL). The resulting solution was left under stirring for 4 days at 20° C. Then an NaHCO₃ aqueous saturated solution was added until pH 7, to obtain a precipitate which was filtered. After concentration of the solution, a second amount of precipitate was obtained. The two samples were combined and dried (50° C.; 1.3 kPa), to, give the desired product (2 g; 3.7 mmol). Yield 87%.

m.p.: 173° C.

B) N-[2-[bis[2-(1,1-dimethylethoxy)-2-oxoethyl]amino]-ethyl]-N-[2-(1,1-dimethylethoxy)-2-oxoethyl]-O-(4-hydroxyphenyl)-3,5-diiodo-L-tyrosine methyl ester

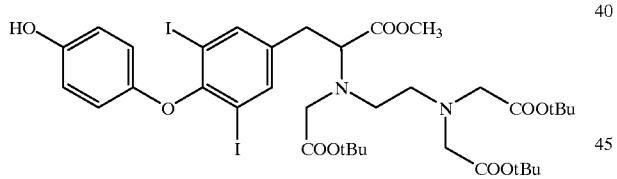

The compound was prepared from the intermediate obtained in the previous step, according to the process reported in Schemes 4A and 4B of the general disclosure.

C) N-[2-[bis(carboxymethyl)amino]ethyl]-N-(carboxymethyl)-O-(4-hydroxyphenyl)-3,5-diiodo-L-tyrosine

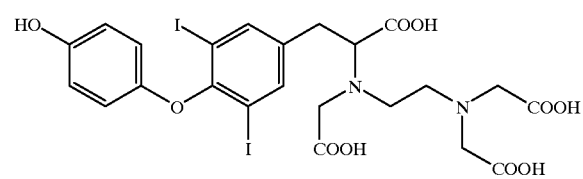

The product was obtained from the tetraester of the above step by hydrolysis with 0.25 M H₂SO₄ at 90° C., followed by treatment with NaOH to pH 13.5 and r.t.

D) Manganese complex of N-[2-[bis(carboxymethyl)aminoethyl]-N-(carboxymethyl)-O-(4-hydroxyphenyl)-3,5-diiodo-L-tyrosine salified with 1-deoxy-1-(methylamino)-D-glucitol (1:2)

The free ligand from the previous step was complexed with MnCl₂ and salified . with 1-deoxy-1-(methylamino)-D-glucitol according to the procedure reported in Scheme 1 of the general disclosure. Overall yield 15%.

EXAMPLE 8

Manganese complex of N,N'-1,2-ethanediylbis [N-(carboxymethyl)-L-tyrosine]salified with 1-deoxy-1-(methylamino)-D-glucitol (1:2)

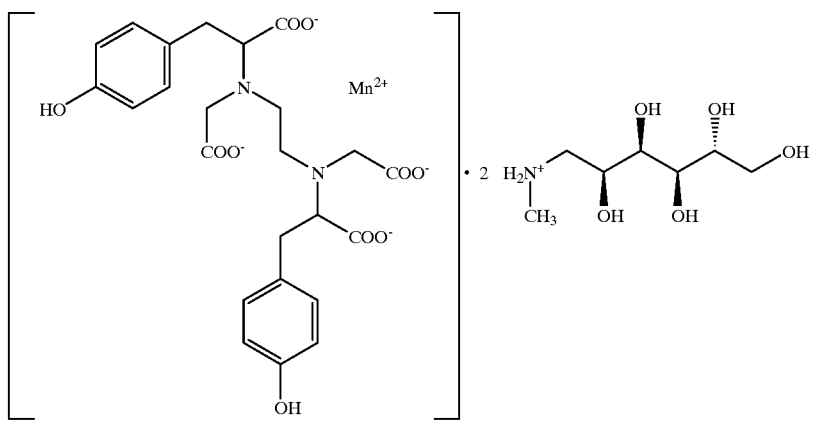

A) N,N'-1,2-ethanediylbis[N-(carboxymethyl)-L-tyrosine]

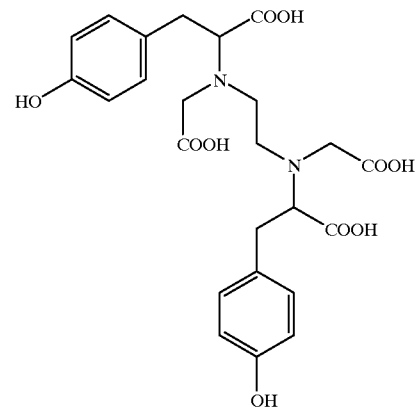

The compound was prepared starting from L-tyrosine, according to the process of example 2.

B) Manganese complex of N,N'-1,2-ethanediylbis[N-(carboxymethyl)-L-tyrosine] salified with 1-deoxy-1-(methylamino)-D-glucitol (1:2).

The free ligand from the previous step was complexed with $MnCl_2$ and salified with 1-deoxy-1-(methylamino)-D-glucitol according to the procedure reported in Scheme 1 of the general disclosure. Overall yield 21%.

EXAMPLE 9

Manganese complex of N,N'-1,2-ethanediylbis[N-(carboxymethyl)-O-(4-hydroxyphenyl)-3,5-diiodo-L-tyrosine] salified with 1-deoxy-1-(methylamino)-D-glucitol (1:2)

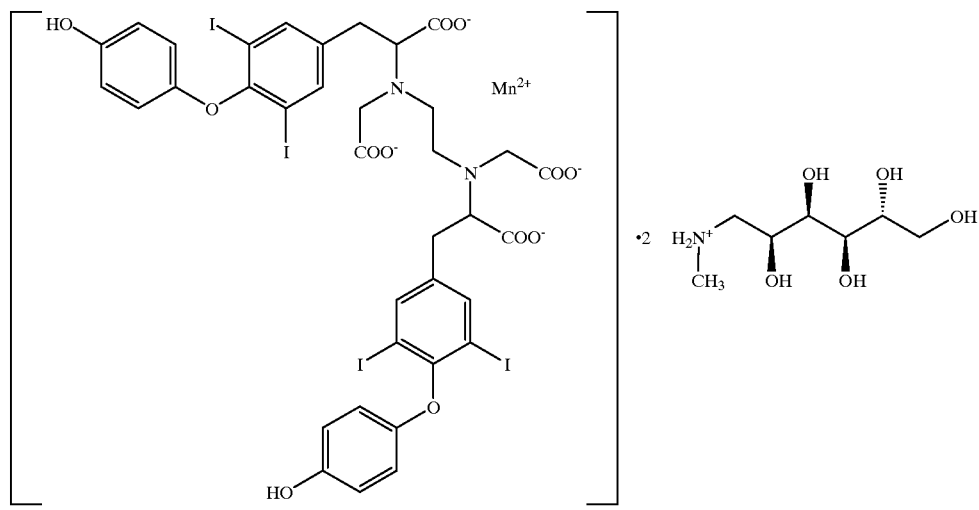

A) N,N'-1,2-ethanediylbis[N-(carboxymethyl)-O-(4-hydroxyphenyl)-3,5-diiodo-L-tyrosine

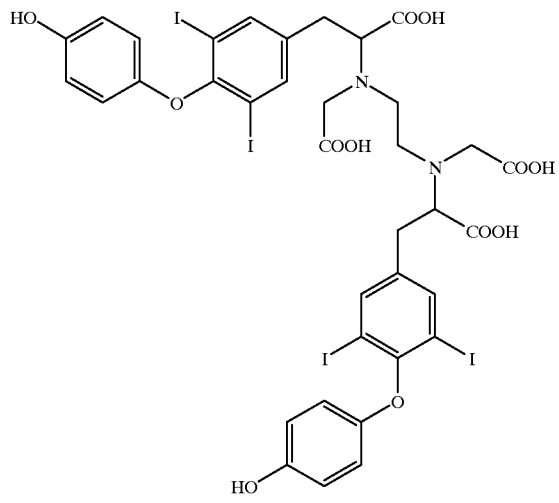

The compound was prepared starting from O-(4-hydroxyphenyl)-3,5-diiodo-L-tyrosine, according to the process of example 2.

B) Manganese complex of N,N'-1,2-ethanediylbis [N-(carboxymethyl)-O-(4-hydroxyphenyl)-3,5-diiodo-L-tyrosine] salified with 1-deoxy-1-(methylamino)-D-glucitol (1:2)

The free ligand from the previous step was complexed with $MnCl_2$ and salified with 1-deoxy-1-(methylamino)-D-glucitol according to the procedure reported in Scheme 1 of the general disclosure. Overall yield 15%.

EXAMPLE 10

Manganese complex of N,N'-1,2-ethanediylbis[N-(carboxymethyl)-L-trypthophan] salified with 1-deoxy-1-(methylamino)-D-glucitol (1:2)

A) N,N'-1,2-ethanediylbis[N-(carboxymethyl)-L-trypthophan

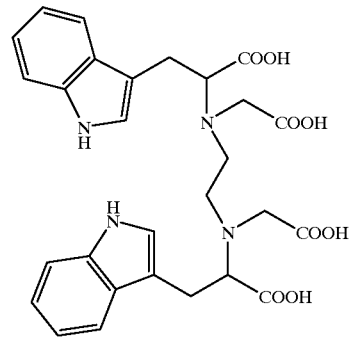

The compound was prepared starting from L-trypthophan (commercial product), according to the process of example 2.

B) Manganese complex of N,N'-1,2-ethanediylbis[N-(carboxymethyl)-L-trypthophan] salified with 1-deoxy-1-(methylamino)-D-glucitol (1:2)

The free ligand from the previous step was complexed with $MnCl_2$ and salified with 1-deoxy-1-(methylamino)-D-glucitol according to the procedure reported in Scheme 1 of the general disclosure. Overall yield 25%.

The relaxivity of the compounds of the invention was measured both in saline solution and in human serum, reconstituted from Seronorm$^{(R)}$ Human (Nycomed Pharma), lyophilized human serum, and the resulting data are summarized in TABLES 1 and 2.

TABLE 1 reports the relativity values measured for some compounds of the invention at 20 MHz; the other experimental conditions used are detailed following the table itself. The high relaxivity value obtained in serum clearly shows the remarkable potential of these compounds in M.R.I. diagnostic imaging in which the recorded images are $T_2$ weighed images as well as in the imaging of the cardio-circulatory system.

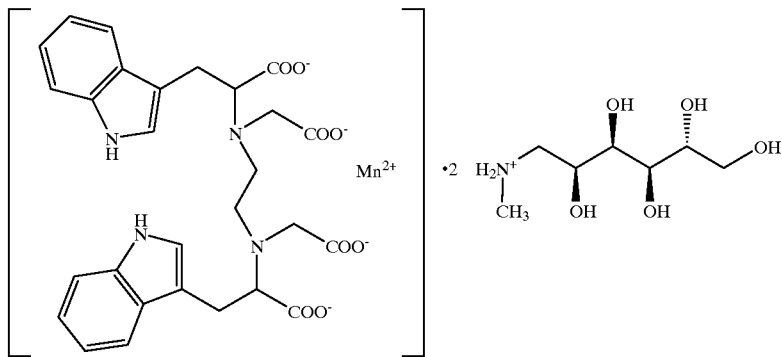

TABLE 1

| | Relaxivity (mM$^{-1}$ s$^{-1}$) | | | |
|---|---|---|---|---|
| | Aqueous solution | | Seronorm ™ Human[1] | |
| Compound | $r_1$ | $r_2$ | $r_1$ | $r_2$ |
| MnCl$_2$ | 6.59[2] | 39.18[2] | 53[3] | 75[3] |
| Mn-DPDP[4] | 2.8[5] | 3.7[5] | | |
| Example 1 | 2.93[6] | 4.45[6] | 15[7] | 19[7] |
| Example 2 | 3.15[6] | 4.25[6] | 27[7] | 36[7] |
| Example 3 | 3.52[6] | 5.09[6] | 43[7] | 56[7] |

[1] Human serum freeze-dried and reconstituted prior to use; available from Nycomed Pharma AS Oslo, Norway.
[2] Data measured on 0.15 M NaCl aqueous solutions; 20 MHz; 39° C.; pH 4.
[3] Data calculated between 0 and 1 mM; 20 MHz; 39° C.; pH 7.0.
[4] JM.R.I. 1993, 179–186.
[5] L.mmol$^{-1}$.s$^{-1}$; 40° C.; 20 MHz; aqueous solution containing 20 mol % calcium ascorbate and 3 eq. of Na$^+$.
[6] Data measured on 0.15 M NaCl aqueous solutions; 20 MHz; 39° C.; pH 7.3.
[7] Data calculated between 0 and 1 mM; 20 MHz; 39° C.

TABLE 2 comprises the results obtained from tests carried out under the same experimental conditions as above and in which $r_1$ and $r_2$ relaxivities were measured in serum and in aqueous solution at lower fields, precisely at 5 and 10 MHz. Said data evidence the significant increase in relaxivity obtained in serum already at 5 MHz and are indicative of the potential advantageous use of the compounds of the invention in M.R.I. diagnostic imaging at low fields.

TABLE 2

| | Relaxivity (mM$^{-1}$s$^{-1}$) | | | | | |
|---|---|---|---|---|---|---|
| | $r_1$ 5 MHz | | $r_1$ 10 MHz | | $r_2$ 10 MHz | |
| Compound | Aqueous solution | Seronorm ™ | Aqueous solution | Seronorm ™ | Aqueous solution | Seronorm ™ |
| Example 1 | 4.3 | 11.8 | 3.7 | 12.8 | 4.3 | 14.8 |
| Example 2 | 4.5 | 19.9 | 3.9 | 26.1 | 4.6 | 31.9 |
| Example 3 | 4.7 | 26.2 | 4.3 | 35.1 | 4.8 | 47.2 |

What is claimed is:

1. A compound of formula (I) in the racemic or optically active form:

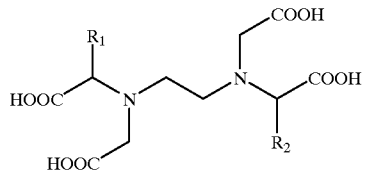

(I)

wherein:
R$_1$, R$_2$ are independently a hydrogen atom, or a straight or branched (C$_1$-C$_{20}$) alkyl chain, saturated or unsaturated, said chain optionally interrupted by one or more nitrogen or sulfur atoms, as well as by —CO—, —CONH—, —NHCO—, —SO—, —SO$_2$—, —SO$_2$NH— groups, or optionally substituted by one or more NH$_2$, OH, halogen, COOH groups and the respective ester or amide derivatives, said chain in any case interrupted or substituted by one or more R$_3$ cyclic residues, which are the same or different, non-fused or fused, provided that, when some of the R$_3$ residues are fused together, the maximum number of rings forming the corresponding polycyclic unit is three, wherein
R$_3$ is a 5- or 6-membered cyclic unit, carbocyclic or heterocyclic, saturated, unsaturated or aromatic, said cyclic units unsubstituted or substituted with one or more R$_4$ groups, which are the same or different, wherein
R$_4$ is OH, halogen, NHR$_5$, N(R$_5$)$_2$, —O—R$_5$, —S—R$_5$, or —CO—R$_5$, wherein the R$_5$ groups, which are the same or different, are straight or branched (C$_1$–C$_5$) alkyl, unsubstituted or substituted with one or more hydroxy and/or alkoxy and/or carboxy groups, or R$_4$ is a COOH group, or an ester or amido derivative thereof, or a —SO$_3$H group or an amido derivative thereof,
or R$_4$ is a —O—R$_6$ group, wherein R$_6$ is a 5- or 6-membered cyclic unit, carbocyclic or heterocyclic, saturated, unsaturated or aromatic, said cyclic unit optionally substituted by one or more OH, halogen, —NHR$_5$, —N(R$_5$)$_2$, —O—R$_5$, —S—R$_5$, —CO—R$_5$ groups, or by one or more —COOH groups, or the ester or amido derivatives thereof, or —SO$_3$H or amido derivatives thereof,
provided that R$_1$ and R$_2$ are not at the same time hydrogen; or a chelate thereof with a manganese ion in an oxidation state +2 (Mn(II)) or a salt thereof with a physiologically compatible organic base selected from a primary, secondary or tertiary amine or a basic amino acid, or with an inorganic base whose cation is sodium, potassium, magnesium, calcium, or mixtures thereof.

2. A compound as claimed in claim 1 wherein R$_1$ and R$_2$, when other than H, are selected from:

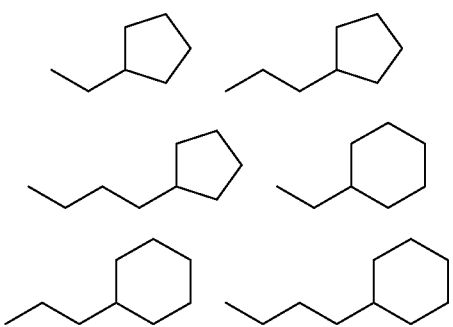

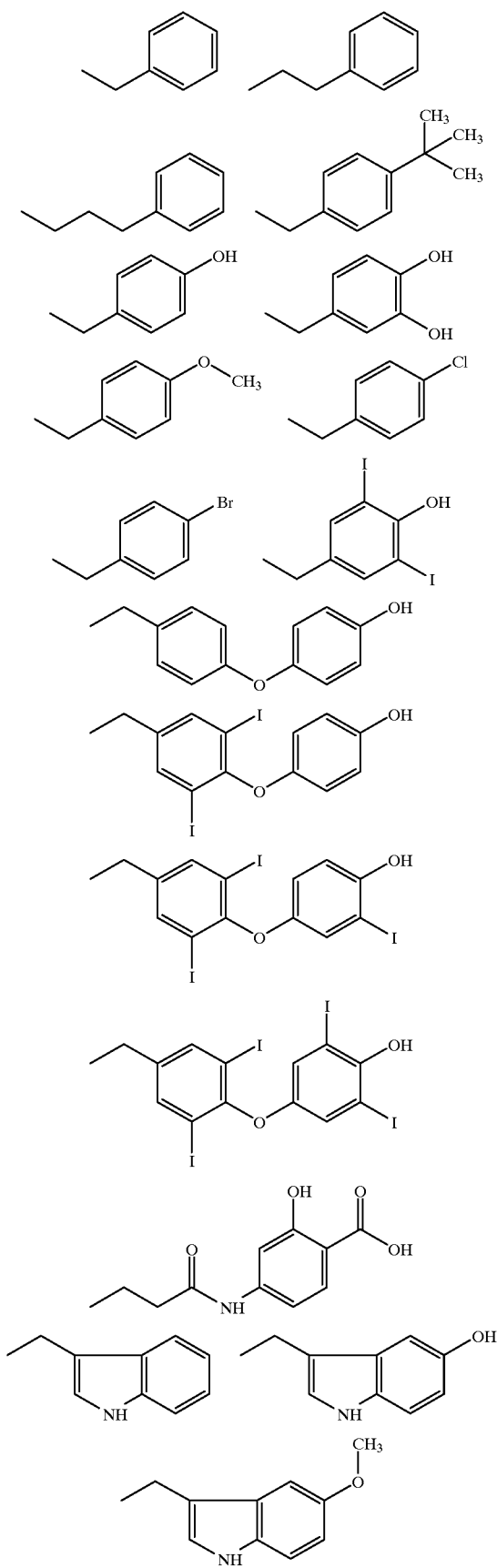
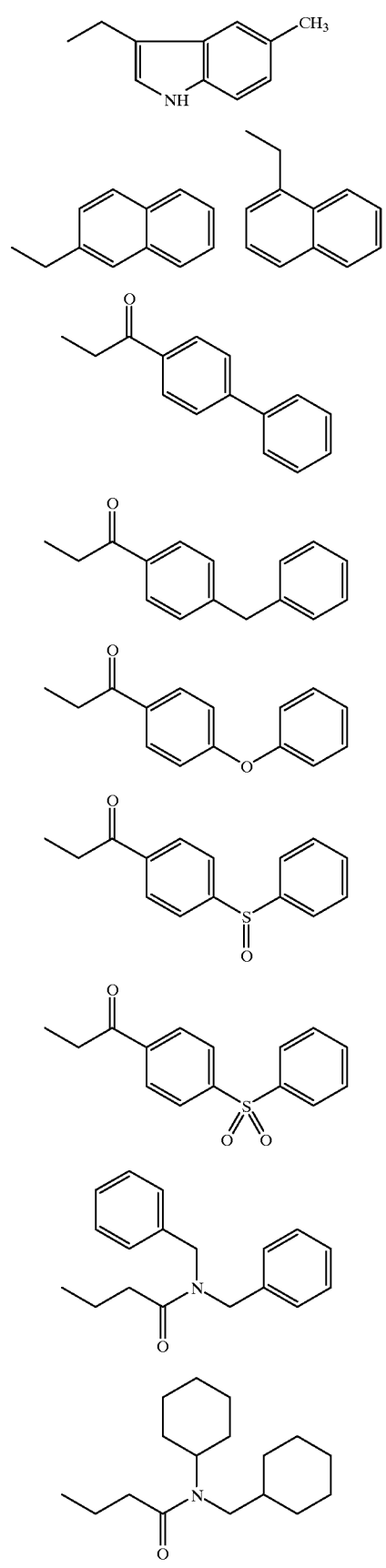

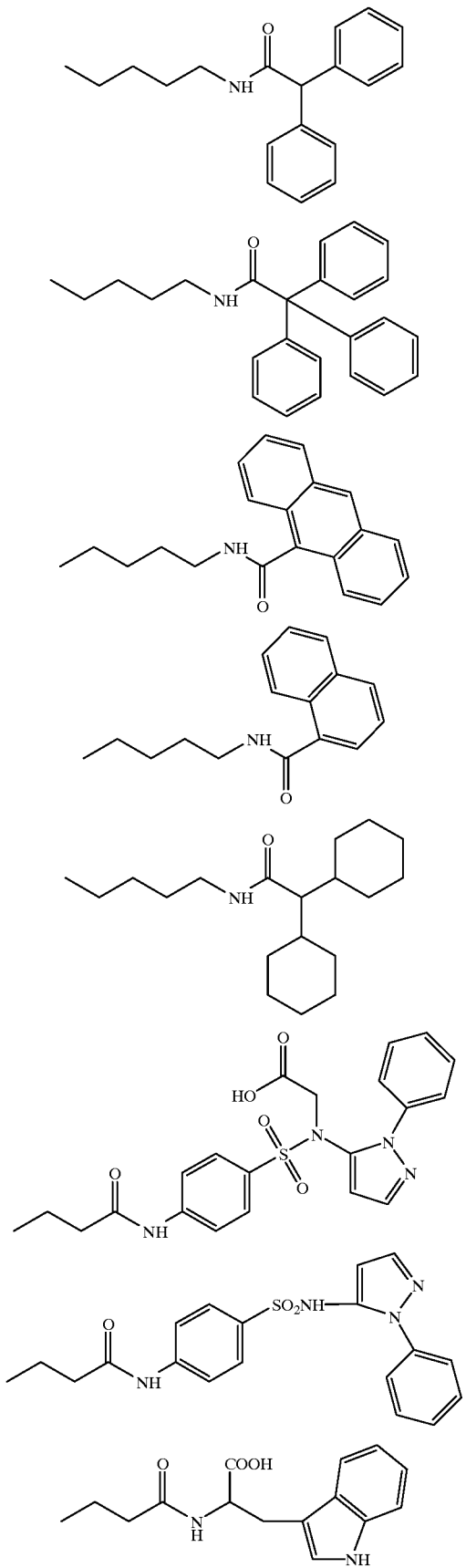

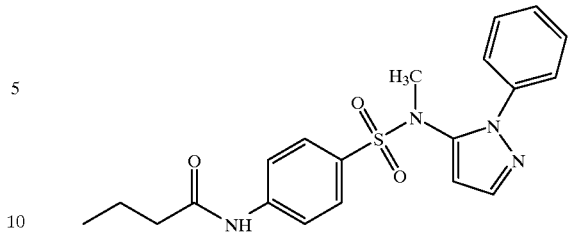

3. A compound of general formula (II), in the racemic or optically active form

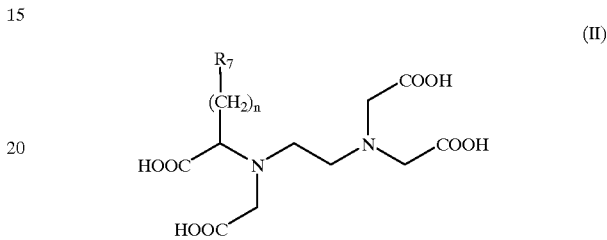

wherein:

R$_7$ is a 5- or 6-membered cyclic unit, carbocyclic or heterocyclic, saturated, unsaturated or aromatic, optionally substituted by one or more groups selected from OH, halogen, COOH or an ester or amido derivative thereof, -SO$_3$H or an amido derivative thereof, or —R$_5$, —NHR$_5$, —N(R$_5$)$_2$, —O—R$_5$, —S—R$_5$, wherein R$_5$ is a straight or branched C$_1$-C$_5$, alkyl, unsubstituted or substituted with one or more hydroxy, alkoxy or carboxy groups or from a group selected from —O—R$_8$ and —CH$_2$R$_8$ wherein R$_8$ is a further 5- or 6-membered cyclic unit, carbocyclic or heterocyclic, saturated, unsaturated or aromatic, optionally substituted by one or more groups selected from OH, COOH and halogen; and n=1–6;

or a chelated complex salt of the compound of general formula (II) with a manganese ion in the oxidation state +2 (Mn(II)) and a salt thereof with physiologically compatible organic base selected from a primary, secondary or tertiary amine or a basic amino acid, or with an inorganic base whose cation is sodium, potassium, magnesium, or calcium or mixtures thereof.

4. A compound of general formula (III), both in a racemic or optically active form

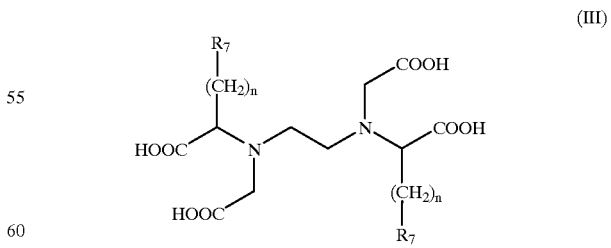

wherein:

R$_7$ is a 5- or 6-membered cyclic unit, carbocyclic or heterocyclic, saturated, unsaturated or aromatic, optionally substituted by one or more groups selected from OH, halogen, COOH or an ester or amido derivative thereof, —SO₃H or an amido derivative thereof, or —R₅, —NHR₅, —N(R₅)₂, —O—R₅, —S—R₅, wherein R₅ is a straight or branched C₁–C₅ alkyl, unsubstituted or substituted with one or more hydroxy, alkoxy or carboxy groups, or by a group selected from —O—R₈ and —CH2R8 wherein R8 is a further 5- or 6-membered cyclic unit, carbocyclic or heterocyclic, saturated, unsaturated or aromatic, optionally substituted by one or more groups selected from OH, COOH and halogen; and n=1–6;

or a chelated complex salt of the compound of general formula (III) with a manganese ion in the oxidation state +2 (Mn(II)) and a salt thereof with physiologically compatible organic base selected from a primary, secondary or tertiary amine or basic amino acid, or with an inorganic base whose cation is sodium, potassium, magnesium or calcium or mixtures thereof.

5. A compound of general formula (IV), in a racemic or optically active form:

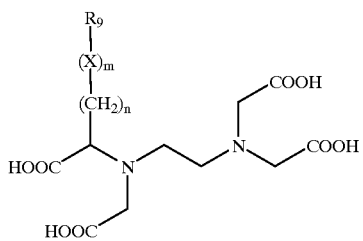

(IV)

wherein:

R₉ is a group of 2 or 3 cyclic units, non-fused or fused, which are the same or different, wherein said unit is carbocyclic, heterocyclic, saturated, unsaturated or aromatic;

n=1–6;
m=0 or 1; and
X=—NHCO, —CONH, —CONH—CH₂—, or a chelated complex salt of the compound of general formula (II) with a manganese ion in the oxidation state +2 (Mn(II)) and a salt thereof with a physiologically compatible organic base selected from a primary, secondary, or tertiary amine or a basic amino acid, or with an inorganic base whose cation is sodium, potassium, magnesium, or calcium or mixtures thereof.

6. A compound of general formula (V), in a racemic or optically active form:

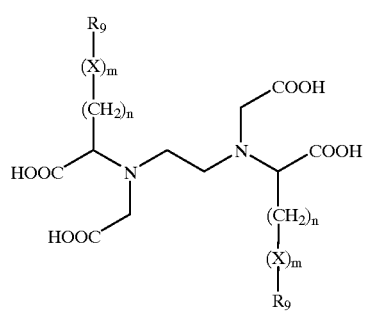

(V)

wherein:

R₉ is a group of 2 or 3 cyclic units, non-fused or fused, which are the same or different, wherein said unit is carbocyclic, heterocyclic, saturated, unsaturated or aromatic and n=1–6;
m=0 or 1; and
X=—NHCO, —CONH, —CONH—CH₂—.

or a chelated complex salt of the compound of general formula (II) with a manganese ion in the oxidation state +2 (Mn(II)) and a salt thereof with a physiologically compatible organic base selected from a primary, secondary, or tertiary amine or a basic amino acid, or with an inorganic base whose cation is sodium, potassium, magnesium, or calcium or mixtures thereof.

7. A compound according to claim 3 and 4 wherein R₇ is cyclohexyl, phenyl, hydroxyphenyl or a 3,5-diiodothyronine residue.

8. A compound according to claim 5 or 6 wherein R₉ is naphthalene, anthracene or indole and X is —NHCO.

9. A compound according to claim 1 in which the physiologically compatible organic base is 1-deoxy-1-(methylamino)-D-glucitol.

10. A chelated complex salt selected from:

manganese complex of N-[2-[bis(carboxymethyl)amino]ethyl]-N-(carboxymethyl)-D-phenylalanine salified with 1-deoxy-1-(methylamino)-D-glucitol;

manganese complex of [N,N'-1,2-ethanediylbis[N-(carboxymethyl)-L-phenylalanine]] salified with 1-deoxy-1-(methylamino)-D-glucitol;

manganese complex of [S—(R*,R*)]-α,α'-[1,2-ethanediylbis-[(carboxymethyl)imino]]bis(cclohexanepropanoic)acid salified with 1-deoxy-1-(methylamino)-D-glucitol;

manganese complex of N²-[2-[bis(carboxymethyl)amino]ethyl]-N²-(carboxymethyl)-N⁶-[(9-anthrace-nyl)carbonyl]-L-lysine salified with 1-deoxy-1-(methylamino)-D-glucitol;

manganese complex of N²-[2-[bis(carboxymethyl)-amino]ethyl]-N²-(carboxymethyl)-N⁶-[(1-naphthyl)carbonyl]-L-lysine salified with 1-deoxy-1-(methylamino)-D-glucitol;

manganese complex of N-[2-[bis(carboxymethyl)amino]ethyl]-N-(carboxymethyl)-L-tyrosine salified with 1-deoxy-1-(methylamino)-D-glucitol;

manganese complex of N-[2-[bis(carboxymethyl)amino]ethyl]-N-(carboxymethyl)-O-(4-hydroxyphenyl)-3,5-di-iodo-L-tyrosine salified with 1-deoxy-1-(methylamino)-D-glucitol;

manganese complex of N,N'-1,2-ethanediylbis [N-(carboxymethyl)-L-tyrosine] salified with 1-deoxy-1-(methylamino)-D-glucitol;

manganese complex of N,N'-1,2-ethanediylbis [N-(carboxymethyl)-O-(4-hydroxyphenyl)-3,5-diiodo-L-tyrosi-ne] salified with 1-deoxy-1-(methylamino)-D-glucitol; or manganese complex of N,N'-1,2-ethanediylbis[N-(carboxymethyl)-L-tryptophan] salified with 1-deoxy-1-(methylamino)-D-glucitol.

11. A contrastographic composition for M.R.I. diagnostic imaging comprising at least one chelate according to claim 1 or a physiologically compatible salt thereof.

12. The contrastographic formulation as claimed in claim 11 for recording images of organs or tissues of human or animal bodies.

13. A method of MRI diagnostic imaging organs of a human or animal body using the composition of claim 11.

14. The method as claimed in claim 13 wherein a magnetic field used for recording said images ranges from 0.5 to 2 Tesla.

15. The method claimed in claim 14 wherein said images are acquired by T1 weighed sequences or T2 weighed sequences or combinations thereof.

16. The method as claimed in claim 15 wherein said images are acquired by T2 weighed sequences.

17. The composition as claimed in claim 11 which contains said chelate in a concentration ranging from 0.001 to 1.0 mmol/mL.

18. The composition as claimed in claim 17 which contains said chelate in a concentration ranging from 0.01 to 0.5 mmol/ml.

19. The method as claimed in claim 13 in which the chelate is administerde to the patient in doses ranging from 0.001 to 0.1 mmol/kg.

* * * * *